US012631654B2

(12) United States Patent
Shenhar-Tsarfaty et al.

(10) Patent No.: US 12,631,654 B2
(45) Date of Patent: May 19, 2026

(54) NON-INVASIVE ASSAY FOR DETECTING AND MONITORING SYSTEMIC INFLAMMATION

(71) Applicants: ICHILOV TECH LTD., Tel Aviv (IL); YEDA RESEARCH AND DEVELOPMENT CO. LTD., Rehovot (IL)

(72) Inventors: Shani Shenhar-Tsarfaty, Kibbutz Gesher (IL); Shlomo Avraham Berliner, Givataim (IL); Ori Rogowski, Tel Aviv (IL); Eyal Fisher, Hod Hasharon (IL); Adi Silberman, Tel Aviv (IL); Yishai Levin, Yavne (IL)

(73) Assignees: ICHILOV TECH LTD., Tel Aviv (IL); YEDA RESEARCH AND DEVELOPMENT CO. LTD., Rehovot (IL)

( * ) Notice: Subject to any disclaimer, the term of this patent is extended or adjusted under 35 U.S.C. 154(b) by 1023 days.

(21) Appl. No.: 17/781,706

(22) PCT Filed: Dec. 10, 2020

(86) PCT No.: PCT/IL2020/051278
§ 371 (c)(1),
(2) Date: Jun. 1, 2022

(87) PCT Pub. No.: WO2021/117045
PCT Pub. Date: Jun. 17, 2021

(65) Prior Publication Data
US 2023/0003742 A1 Jan. 5, 2023

Related U.S. Application Data

(60) Provisional application No. 62/946,438, filed on Dec. 11, 2019.

(51) Int. Cl.
*G01N 33/68* (2006.01)

(52) U.S. Cl.
CPC ..... *G01N 33/6893* (2013.01); *G01N 33/6848* (2013.01); *G01N 2800/56* (2013.01); *G01N 2800/7095* (2013.01)

(58) Field of Classification Search
CPC ........... G01N 33/6893; G01N 33/6803; G01N 33/6848; G01N 2800/7095; G01N 2800/52; G01N 2800/56
USPC ........................................................ 436/173
See application file for complete search history.

(56) References Cited

U.S. PATENT DOCUMENTS

| | | | |
|---|---|---|---|
| 4,313,734 A | 2/1982 | Leuvering | |
| 4,376,110 A | 3/1983 | David | |
| 4,632,901 A | 12/1986 | Valkirs | |
| 4,786,589 A | 11/1988 | Rounds | |
| 4,816,567 A | 3/1989 | Cabilly | |
| 5,189,178 A | 2/1993 | Galardy | |
| 5,239,078 A | 8/1993 | Galardy | |
| 5,656,448 A | 8/1997 | Kang | |
| 9,200,324 B2 | 12/2015 | Cavet | |
| 9,726,668 B2 | 8/2017 | Oved et al. | |
| 2003/0036070 A1 | 2/2003 | Chakravarti | |
| 2004/0096917 A1* | 5/2004 | Ivey | C12Q 1/6837 435/7.32 |
| 2009/0280108 A1 | 11/2009 | Gong | |
| 2011/0137851 A1 | 6/2011 | Cavet | |
| 2014/0162370 A1* | 6/2014 | Ling | G01N 33/6893 436/86 |
| 2015/0038595 A1 | 2/2015 | Anderberg | |
| 2015/0045245 A1 | 2/2015 | Vanpoucke | |
| 2015/0203899 A1 | 7/2015 | Levin et al. | |
| 2015/0293131 A1* | 10/2015 | Anderberg | G01N 33/6893 435/7.92 |
| 2017/0269081 A1 | 9/2017 | Oved | |
| 2019/0049443 A1* | 2/2019 | Eastman | G16B 40/20 |
| 2019/0144943 A1 | 5/2019 | Khatri et al. | |
| 2019/0323065 A1 | 10/2019 | Levin et al. | |
| 2020/0249243 A1* | 8/2020 | Hwang | G01N 33/6893 |
| 2020/0255898 A1 | 8/2020 | Deirmengian | |

FOREIGN PATENT DOCUMENTS

| | | |
|---|---|---|
| EP | 0125118 B1 | 9/1992 |
| EP | 2711710 B1 | 4/2017 |
| WO | 2006071583 A2 | 7/2006 |
| WO | 2016079219 | 5/2016 |
| WO | 2016081941 | 5/2016 |
| WO | 2018035563 | 3/2018 |
| WO | 2019027910 A2 | 2/2019 |

OTHER PUBLICATIONS

Yakar, S. et al, Seminars in Arthritis and Rheumatism 1995, 24, 255-261. (Year: 1995).*
Urieli-Shoval, S. et al, Current Opinion in Hematology 2000, 7, 64-69. (Year: 2000).*
Mayer, J. M. et al, British Journal of Surgery 2002, 89, 163-171. (Year: 2002).*
Lannergard, A. et al, Journal of Urology 2003, 170, 804-806. (Year: 2003).*
Kentsis, A. et al, Annals of Emergency Medicine 2010, 55, 62-70. e4. (Year: 2010).*

(Continued)

*Primary Examiner* — Arlen Soderquist
(74) *Attorney, Agent, or Firm* — Greenberg Traurig, LLP

(57) ABSTRACT

The invention provides assays and methods for detecting and monitoring systemic inflammation. Particularly, the invention in embodiments thereof relates to the use of urinary biomarkers for non-invasive determination of the level of inflammation.

5 Claims, 4 Drawing Sheets

Specification includes a Sequence Listing.

(56) References Cited

OTHER PUBLICATIONS

Ling, X. B. et al, Clinical Proteomics 2010, 6, 175-193. (Year: 2010).*

Lu, J. et al, Proceedings of the National Academy of Sciences 2014, 111, 5189-5194. (Year: 2014).*

Stalmach, A. et al, PLOS One 2014, 9, article e104625, 9 pages. (Year: 2014).*

Targonska-Stepniak, B. et al, Mediators of Inflammation 2014, Article 793628, 7 pages. (Year: 2014).*

Azurmendi, L. et al, Journal of Proteome Research 2015, 14, 3948-3956. (Year: 2015).*

Hwang, Y. G. et al, Arthritis Research & Therapy 2016, 18, Article 108, 8 pages. (Year: 2016).*

Siebert, S. et al, Scientific Reports 2017, 7, Article 40473, 9 pages. (Year: 2017).*

Seok, A. et al, Molecules 2017, 22, Article 805, 13 pages. (Year: 2017).*

Belczacka, I. et al, Scientific Reports 2018, 8, article 5227, 11 pages. (Year: 2018).*

Kelly, B. J. et al, Clinical Investigations 2018, 46, 1106-1113. (Year: 2018).*

Jortani et al (2019) sensitive noninvasive marker for the diagnosis of probable bacterial or viral infection, J Clin Lab Anal 18(6): 289-295.

Lyndon et al (2019) Validation of a host response test to distinguish bacterial and viral respiratory infection, EBioMedicine 48: 453-461.

Oved et al (2015) A novel host-proteome signature for distinguishing between acute bacterial and viral infections, PLoS One 10(3): e0120012.

Sweeney et al (2016) Robust classification of bacterial and viral infections via integrated host gene expression diagnostics, Sci Transl Med. Author manuscript, available in PMC Mar. 14, 2017. Pubished iin final edited form as: Sci Transl Med. Jul. 6, 2016; 8(346): 346ra91.

Valim et al (2016) Responses to Bacteria, Virus, and Malaria Distinguish the Etiology of Pediatric Clinical Pneumonia, Am J Respir Crit Care Med 193(4): 558-459.

Ashkenazi-Hoffnung et al., (2018) A host-protein signature is superior to other biomarkers for differentiating between bacterial and viral disease in patients with respiratory infection and fever without source: a prospective observational study. Eur J Clin Microbiol Infect Dis 37(7): 1361-1371.

Denz et al., (1990) Value of urinary neopterin in the differential diagnosis of bacterial and viral infections. Klin Wochenschr 68(4): 218-222.

Gannon et al., (2019) A point-of-care assay for alpha-1-acid glycoprotein as a diagnostic tool for rapid, mobile-based determination of inflammation. Curr Res Biotechnol 1: 41-48.

Jain KK (2017) Biomarkers of Infectious Diseases. In: The Handbook of Biomarkers. Humana Press, New York, NY. pp. 219-238.

Jortani et al., (2004) Sensitive noninvasive marker for the diagnosis of probable bacterial or viral infection. J Clin Lab Anal 18(6): 289-295.

Merrifield (1963) Solid Phase Peptide Synthesis. I. The Synthesis of a Tetrapeptide. J Am Chem Soc 85)14): 2149-2154.

Oveland et al., (2012) Proteomic evaluation of inflammatory proteins in rat spleen interstitial fluid and lymph during LPS-induced systemic inflammation reveals increased levels of ADAMST1. J Proteome Res 11(11): 5338-5349.

Reisinger et al., (2014) Non-invasive serum amyloid A (SAA) measurement and plasma platelets for accurate prediction of surgical intervention in severe necrotizing enterocolitis (NEC). PLoS One 9(6): e90834.

Rodríguez-Ortiz et al., (2018) Novel Urinary Biomarkers For Improved Prediction Of Progressive Egfr Loss In Early Chronic Kidney Disease Stages And In High Risk Individuals Without Chronic Kidney Disease. Sci Rep 8(1): 15940 with erratum.

Whetton et al., (2020) Proteomics and Informatics for Understanding Phases and Identifying Biomarkers in COVID-19 Disease. J. Proteome Res 19(11): 4219-4232.

* cited by examiner

NON-INVASIVE ASSAY FOR DETECTING AND MONITORING SYSTEMIC INFLAMMATION

CROSS-REFERENCE TO RELATED APPLICATIONS

This application is the U.S. National Stage of International Patent Application No. PCT/IL2020/051278, filed on Dec. 10, 2020, which claims the benefit of and priority to U.S. Provisional Patent Application No. 62/946,438, filed on Dec. 11, 2019, the contents of each of which are hereby incorporated by reference in their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 706 byte ASCII (text) file named "Seq_List" created on Dec. 10, 2020.

FIELD OF THE INVENTION

The invention provides assays and methods for detecting and monitoring systemic inflammation. Particularly, the invention in embodiments thereof relates to the use of urinary biomarkers for non-invasive evaluation of the level of inflammation.

BACKGROUND OF THE INVENTION

The biological response of body tissues to injury, infection or irritation is typically characterized by inflammation, an innate immune reaction in which a cascade of cellular and microvascular events serves to eradicate the infection, remove damaged tissue and generate new tissue. During this process, elevated permeability in microvessels allows neutrophils and mononuclear cells to leave the intravascular compartment, and perform various anti-microbial activities to eradicate the injury. Inflammation can be characterized as local or systemic, and as acute or chronic, depending on its specific etiology and course.

Sepsis is a clinical syndrome that complicates severe infection, which is characterized by a dysregulated, systemic inflammation, and may progress to increasingly severe tissue injury, organ failure and death. Septic shock is a severe form of sepsis, with significantly increased mortality due to increased abnormalities of circulation and/or cellular metabolism. Early recognition and treatment of sepsis is key to improved survival, as the source of infection, which is most often bacterial, should be controlled as early as possible.

The concept of the systemic inflammatory response syndrome (SIRS), defined by certain abnormalities of vital signs and laboratory results, has been introduced in 1992, to define a clinical response to a non-specific insult, wherein SIRS accompanied by a documented or presumed infection has been defined as sepsis. However, SIRS criteria have been found to lack sensitivity and specificity for increased mortality risk, which is the main consideration for using such a conceptual model. Blood levels of certain cytokines and acute phase proteins (APPs), and in particular C-reactive protein (CRP), are also used to evaluate the level of systemic inflammation.

APPs are plasma proteins, the synthesis and the circulating concentrations of which are adaptively regulated in response to most forms of inflammation, infection and tissue injury. The acute-phase response is considered part of the innate immune system, and APPs play a role in mediating such systemic effects as fever, leukocytosis, increased cortisol, decreased thyroxine, decreased serum iron, and many others. APPs can be categorized as positive (increasing serum concentration, e.g. CRP, complement factors, serum amyloid A and ferritin) or negative (decreasing serum concentration, e.g. albumin, transferrin, and transthyretin).

The development of methods for assessing inflammatory load in a subject, comprising immunoassays that examine protein marker levels in blood samples, is an ongoing effort, and various diagnostic assays are under development.

WO 2019/027910 suggests an adjusted multi-biomarker disease activity score for inflammatory disease assessment, in particular in rheumatoid arthritis. Specifically, provided are methods for assessing response to inflammatory disease therapy. The methods include performing immunoassays to generate scores based on quantitative data for expression of inflammatory biomarkers to assess disease activity in an inflammatory disease such as rheumatoid arthritis.

U.S. Pat. No. 9,200,324 is directed to biomarkers useful for diagnosing and assessing inflammatory disease, in particular rheumatoid arthritis, along with kits for measuring their expression. Also provided are predictive models based on the biomarkers, as well as computer systems, and software embodiments of the models for scoring and optionally classifying samples.

EP 1836493 relates to a method for assigning a therapy regimen and/or assigning a prognosis to a subject diagnosed with or suspected of suffering from SIRS, sepsis, severe sepsis, septic shock, or MODS, comprising: performing an assay method on a sample from said subject that provides one or more detectable signals related to the presence or amount of one or more subject-derived markers, and correlating the signal(s) obtained from said assay method to ruling in or out a therapy regimen for said subject and/or assigning a prognosis to said subject. In particular, the publication discloses the evaluation of various panels of blood markers.

Ashkenazi-Hoffnung et al. 2018 (Eur J Clin Microbiol Infect Dis. July; 37(7):1361-1371) discloses a host-protein signature for differentiating between bacterial and viral disease in patients with respiratory infection and fever without source, based on a combining of three blood proteins: tumor necrosis factor-related apoptosis-inducing ligand (TRAIL), interferon gamma induced protein-10 (IP-10), and C-reactive protein (CRP). US 2017/0269081 relates to a method of determining an infection type in a subject comprising measuring the concentration of a first determinant selected from a first group of determinants and a second determinant selected from a second group of determinants in a sample derived from the subject, wherein said concentration is indicative of the infection type. In particular, the publication discloses the identification of expression profiles of multiple determinants measured in blood serum samples, including TRAIL, IP-10 and CRP.

Urinary biomarkers have also been investigated for diagnostic applications, especially to detect or evaluate renal injury or disease. For example, US 2015/0038595 relates to methods and compositions for diagnosis and prognosis of renal injury and renal failure, and Rodriguez-Ortiz et al., (2018, Sci Rep 8(1): 15940) relates to urinary biomarkers for chronic kidney disease. Certain urinary proteins were also evaluated as markers in the context of infective diseases, for example in EP 2711710, Jortani et al. (2004, J Clin Lab Anal.; 18(6):289-95), Denz et al. (1990, Klin Wochenschr. February 15; 68(4):218-22), and Whetton et al. (2020, J Proteome Res acs.jproteome.0c00326). Evaluation of urinary proteins as potential biomarkers in neonates has been reported, for example, by Reisinger et al. (PLoS One 9.3 (2014)), suggesting urinary SAA as a marker in differentiating severe necrotizing enterocolitis (NEC) from moderate NEC in neonates, particularly if combined with serum platelet count. The significance of these findings outside of the context of neonate NEC and the functionally immature neonate kidney is unclear.

However, despite the need for developing simple and non-invasive diagnostic assays, there is currently no test for assessment of inflammation based on the identification of urinary proteins in adult subjects in clinical practice. In particular, the levels of blood proteins, including those proposed as biomarkers for inflammatory conditions, do not correlate closely with their levels in urine. This may be attributed to processes such as glomerular filtration and tubular absorption in the mature kidney, responsible for restricting the release of most plasma proteins into the blood.

There remains an unmet need for a noninvasive and rapid methods, for ascertaining the level of systemic inflammation in a subject. The ability to determine treatment urgency and immediately treat patients with the urgent need for therapy, as well as to determine the therapeutic efficiency during treatment, by simple assays suitable for self-use, would be highly advantageous.

SUMMARY OF THE INVENTION

The invention provides assays and methods for detecting and monitoring systemic inflammation. Particularly, the invention in embodiments thereof relates to the use of urinary biomarkers for early and non-invasive determination of the grade or intensity of inflammation, and for evaluation of risks associated therewith.

The invention is based, in part, on the surprising discovery of unique proteomic signatures based on measurements of protein biomarkers in the urine, determined to be unexpectedly effective for evaluating systemic inflammation. Surprisingly, as demonstrated herein, diagnostic markers and classifiers were developed, capable of identifying severe systemic inflammation. Further, as demonstrated herein, highly predictive models were constructed, capable of assessing the level of systemic inflammation not only in high-grade severe cases, but also in patients exhibiting signs of mild and moderate inflammation. In contradistinction, it was found that other proteins hitherto used or suggested as blood markers, including tumor necrosis factor-related apoptosis-inducing ligand (TRAIL) and CXCL10 (IP-10), are not appropriate for use as urinary markers.

The invention is further based, in part, on the discovery that certain gene products are present in urine samples in the form of endogenous peptides, rather than as full-length polypeptides that may be found in other samples such as blood. Surprisingly, a serum amyloid A2 (SAA2)-derived peptide was identified, capable of reflecting the level of systemic inflammation with high accuracy.

Thus, the results provide for the detection and monitoring of alterations in the level of systemic inflammation, useful e.g. for disease prognosis, for early identification of subjects that are at enhanced risk of developing disease complications and for evaluating treatment efficacy. The results presented herein enable self-detection of patients at risk to develop acute phase inflammatory response, such as sepsis patients, as well as patients with e.g. rheumatic and autoimmune diseases who are at risk of developing inflammatory outbreaks and disease relapse, without the need to draw blood.

Accordingly, disclosed herein are non-invasive diagnostic assays and methods, useful for the diagnosis, prognosis, monitoring and management of systemic inflammation and conditions associated therewith.

According to embodiments of the invention, provided are methods of analyzing a urine sample. In some embodiments, the methods of the invention comprise the step of determining, in a urine sample of a subject, the levels of at least one, and typically a plurality of protein markers (e.g. three or more gene products) selected from Table 1, as detailed below. Tables 4-6 and 9-14 provide the details of specific biomarker combinations selected from the gene products of Table 1, as detailed in the Examples section below.

TABLE 1

| urinary biomarkers | |
|---|---|
| Gene | Gene product |
| ACY1 | Aminoacylase-1 |
| ADAMTS1 | A disintegrin and metalloproteinase with thrombospondin motifs 1 |
| CFB | Complement factor B |
| CHGA | Chromogranin-A |
| CRP | C-reactive protein |
| CST6 | Cystatin-M |
| EFEMP1 | EGF-containing fibulin-like extracellular matrix protein 1 |
| F9 | Coagulation factor IX |
| GALNS | N-acetylgalactosamine-6-sulfatase |
| GPR56 | G-protein coupled receptor 56 |
| GPX3 | Glutathione peroxidase 3 |
| GUCA2B | Guanylate cyclase activator 2B |
| HIST1H1D | Histone H1.3 |
| LRG1 | Leucine-rich alpha-2-glycoprotein |
| PLAU | Urokinase-type plasminogen activator |
| PTMA | Prothymosin alpha |
| SAA1 | Serum amyloid A-1 protein |
| SAA2 | Serum amyloid A-2 protein |
| SERPINA1 | Alpha-1-antitrypsin |
| SLC28A1 | Sodium/nucleoside cotransporter 1 |
| SLC38A10 | Putative sodium-coupled neutral amino acid transporter 10 |
| SMIM5 | Small integral membrane protein 5 |
| VSIG4 | V-set and immunoglobulin domain-containing protein 4 |
| SRGN | Serglycin |
| ASGR1 | Asialoglycoprotein receptor 1 |
| IGLV3-12 | Human Immunoglobulin lambda variable 3-12 |
| GPC4 | Glypican-4 |
| ABRACL | Costars family protein ABRACL |
| ASAH1 | Acid ceramidase; Acid ceramidase subunit alpha; Acid ceramidase subunit beta |
| ATP6AP1 | V-type proton ATPase subunit S1 |
| C1S | Complement C1s subcomponent; Complement C1s subcomponent heavy chain; Complement C1s subcomponent light chain |
| CD177 | CD177 antigen |
| CRHBP | Corticotropin-releasing factor-binding protein |
| CTSH | Pro-cathepsin H; Cathepsin H mini chain; Cathepsin H; Cathepsin H heavy chain; Cathepsin H light chain |
| DDT; DDTL | D-dopachrome decarboxylase; D-dopachrome decarboxylase-like protein |
| DLK1 | Protein delta homolog 1; Fetal antigen 1 |
| EZR | Ezrin |
| FCGBP | IgGFc-binding protein |
| FCN2 | Ficolin-2 |
| GPC4 | Glypican-4; Secreted glypican-4 |
| GSTO1 | Glutathione S-transferase omega-1 |
| HLA-DPA1 | HLA class II histocompatibility antigen, DP alpha 1 chain |

TABLE 1-continued urinary biomarkers

| Gene | Gene product |
|------|-------------|
| HNRNPA3 | Heterogeneous nuclear ribonucleoprotein A3 |
| IGKV2-29 | Immunoglobulin kappa variable 2-29 |
| IL2RA | Interleukin-2 receptor subunit alpha |
| LGALS1 | Galectin-1 |
| LRG1 | Leucine-rich alpha-2-glycoprotein |
| MATN4 | Matrilin-4 |
| MYOZ1 | Myozenin-1 |
| NEB | Nebulin |
| ORM1 | Alpha-1-acid glycoprotein 1 |
| PTGR1 | Prostaglandin reductase 1 |
| S100A1 | Protein S100-A12; Calcitermin |
| SERPINA3 | Alpha-1-antichymotrypsin; Alpha-1-antichymotrypsin His-Pro-less |
| TLN1 | Talin-1 |
| UMOD | Uromodulin; Uromodulin, secreted form |

The levels of the plurality of markers are determined in embodiments of the invention to thereby determine the urinary proteomic signature of the subject with respect to said plurality of markers. The level of each marker may then be compared to reference values, to thereby compare the urinary proteomic signature of said subject to urinary proteomic signatures of control subjects.

Thus, in some embodiments, provided are methods for analyzing a urine sample, comprising:

a. determining the levels of at least three (e.g. 3-5, 5-10 or 10-15) gene products selected from Table 1 in the sample, to thereby obtain the urinary proteomic signature of the subject with respect to the at least three gene products, and b. comparing the level of each gene product to the respective value corresponding to its level in a healthy control urine sample, to thereby obtain the urinary proteomic signature of said subject as compared to the urinary proteomic signature of the control sample.

According to exemplary embodiments, the gene products are selected from any one of Tables 4-6 or 9-14, wherein each possibility represents a separate embodiment of the invention. In a particular embodiment, said gene products are SAA2, SAA1, and GUCA2B gene products.

In one aspect, there is provided a method of detecting the presence or absence of systemic inflammation in a subject in need thereof, comprising:

a. determining, in a urine sample of the subject, the levels of at least three gene products selected from the group consisting of the gene products presented in any one of Tables 6 and 10-14, to thereby obtain the urinary proteomic signature of the subject with respect to the at least three gene products, b. comparing the level of each gene product to the respective value corresponding to its level in a reference control urine sample, to thereby obtain the urinary proteomic signature of said subject as compared to the urinary proteomic signature of the reference control sample.

In one embodiment, the control sample corresponds to a healthy control subject. In another embodiment, a urinary proteomic signature substantially different from the urinary proteomic signature of the healthy control indicates that said subject has systemic inflammation. In another embodiment the control sample corresponds to a healthy control subject, and a urinary proteomic signature characterized by significantly enhanced levels of said gene products compared to their levels in said control sample indicates that said subject has systemic inflammation. In another embodiment the control sample corresponds to a subject with a predetermined level of inflammation (e.g. mild, moderate or severe). In another embodiment the control sample has been obtained from said subject at a time point preceding the time of obtaining the urine sample from said subject (e.g. for monitoring changes in the inflammatory state of said subject). In another embodiment, the method comprises determining the levels of at least five gene products selected from the group consisting of the gene products listed in any one of Tables 6 and 10-14 in the sample, to thereby obtain the urinary proteomic signature of the subject with respect to the at least five gene products. In another embodiment the method comprises determining the levels of all the gene products listed in Table 6 in the sample, to thereby obtain the urinary proteomic signature of the subject with respect to said gene products. In another embodiment the at least three gene products are selected from the group consisting of the gene products listed in any one of Tables 10-14. In another embodiment the method comprises determining the levels of all the gene products listed in Table 10, in Table 11, in Table 12, in Table 13 or in Table 14, in the sample, to thereby obtain the urinary proteomic signature of the subject with respect to said gene products. In another embodiment a urinary proteomic signature characterized by significantly enhanced levels of SAA1, SAA2 and GUCA2B gene products indicates that said subject has severe systemic inflammation.

In another embodiment the method further comprises determining the level of systemic inflammation in said subject. In various embodiments, the inflammation is selected from the group consisting of mild, moderate and severe. In another embodiment, the method further comprises determining treatment for said subject based on the level of systemic inflammation determined. For example, the methods of the invention may be used for assessing the need for hospitalization or other type of treatment or medical intervention. In another embodiment the method further comprises providing said subject with a treatment suitable for the level of systemic inflammation determined. According to certain non-limitative examples, the treatment may comprise antibiotic drugs, anti-inflammatory drugs, immunosuppressants, or corticosteroids. For example, without limitation, determining treatment may comprise determining a suitable dose, wherein e.g. higher doses are used in severe inflammation compared to moderate inflammation, and the dosage may further be reduced for cases of or mild inflammation. In another non-limitative example, more potent immunosuppressive drugs are used in severe cases compared to less severe cases.

In another embodiment, the methods of the invention may be used for providing disease prognosis for said subject. In another embodiment the methods of the invention may be used for assessing the risk for developing inflammation-related complications (e.g. stroke or cardiovascular disease). In another embodiment, the methods of the invention are used for evaluating treatment efficacy and/or safety in said subject. For example, in one embodiment the subject has received an immunostimulatory treatment, and the method is used for assessing the presence of, or the risk for developing, cytokine release syndrome (CRS). In another embodiment, the subject has received an immunosuppressive treatment, and the method is used for determining treatment efficacy (e.g. inhibition of inflammation or autoimmunity). In another embodiment, the method is used for early detection of an infection, e.g. in cancer patients undergoing irradiation or chemotherapy.

In another aspect, there is provided a method of monitoring systemic inflammation in a subject in need thereof, comprising:

a. obtaining from the subject a first urine sample at a first time point, and a second urine sample at a second time point, wherein the first time point precedes the second time point, b. determining the levels of at least three gene products selected from the group consisting of the gene products presented in any one of Tables 6 and 10-14 in each sample, to thereby determine the urinary proteomic signature of the subject with respect to the at least three gene products at said first and second time points, c. comparing the level of each gene product at said first time point to the respective value corresponding to its level at said second time point, to thereby compare the urinary proteomic signature of said subject at said first and second time points, wherein a urinary proteomic signature at the second time point characterized by significantly enhanced levels of the at least three gene products compared to their respective levels at the first time point is indicative of aggravation of systemic inflammation in said subject, and a urinary proteomic signature at the second time point characterized by significantly reduced levels of the at least three gene products compared to their respective levels at the first time point is indicative of amelioration of systemic inflammation in said subject.

In other embodiments, the methods of the invention are used for non-invasively prognosing, evaluating disease progression of, determining and/or adjusting treatment for, a subject afflicted with a condition associated with elevated blood CRP levels.

In another aspect, there is provided a method of non-invasively monitoring the progression of a condition associated with elevated blood CRP levels in a subject in need thereof, comprising:

a. obtaining from the subject a first urine sample at a first time point, and a second urine sample at a second time point, wherein the first time point precedes the second time point, b. determining the levels of at least three gene products selected from the group consisting of the gene products listed in any one of Tables 6 and 10-14 in each sample, to thereby determine the urinary proteomic signature of the subject with respect to the at least three gene products at said first and second time points, c. comparing the level of each gene product at said first time point to the respective value corresponding to its level at said second time point, to thereby compare the urinary proteomic signature of said subject at said first and second time points, wherein a urinary proteomic signature at the second time point characterized by significantly enhanced levels of the at least three gene products compared to their respective levels at the first time point is indicative of aggravation of the condition in said subject, and a urinary proteomic signature at the second time point characterized by significantly reduced levels of the at least three gene products compared to their respective levels at the first time point is indicative of amelioration said condition in said subject.

In another aspect, the invention provides a method of detecting the presence or absence of severe systemic inflammation, comprising:

a. determining, in a urine sample of a subject, the levels of at least three gene products selected from the group consisting of the gene products presented in any one of Tables 4, 5 and 9, to thereby obtain the urinary proteomic signature of the subject with respect to the at least three gene products, b. comparing the level of each gene product to the respective value corresponding to its urinary level in a healthy control subject, to thereby obtain the urinary proteomic signature of said subject as compared to the urinary proteomic signature of the healthy control subject.

In another embodiment, a urinary proteomic signature substantially different from the urinary proteomic signature of the healthy control indicates that said subject has severe systemic inflammation. In another embodiment a urinary proteomic signature characterized by significantly enhanced levels of said gene products compared to their control levels indicates that said subject has severe systemic inflammation. In one embodiment, the gene products are selected from the group consisting of the gene products presented in Table 4, e.g. at least 3, 4 or 5 of the gene products presented in Table 4. In another embodiment, the gene products are selected from the group consisting of the gene products presented in Table 5, e.g. at least 3, 4, 5, 6, 7, 8, 9 or 10 of the gene products presented in Table 5. In a particular embodiment, said gene products comprise SAA2. In another particular embodiment, said gene products comprise SAA1. In another particular embodiment, said gene products comprise SAA1 and SAA2. In another embodiment, the gene products are selected from the group consisting of CHGA, PLAU, SAA1 and SAA2 gene products. In another embodiment, the gene products comprise CHGA, PLAU, SAA1 and SAA2 gene products. In another embodiment, the gene products comprise CHGA, PLAU, and SAA1 gene products.

In another embodiment, said inflammation is associated with blood CRP levels >120 mg/L, and the gene products are selected from the group consisting of the gene products presented in Table 4. In another embodiment the method comprises determining the levels of all the gene products listed in Table 4 in the sample, to thereby obtain the urinary proteomic signature of the subject with respect to said gene products. In another embodiment, said inflammation is associated with blood CRP levels >100 mg/L, and the gene products are selected from the group consisting of the gene products presented in Table 5. In another embodiment the method comprises determining the levels of all the gene products listed in Table 5 in the sample, to thereby obtain the urinary proteomic signature of the subject with respect to said gene products. In another embodiment said inflammation is associated with blood CRP levels >100 mg/L, and the gene products are selected from the group consisting of the gene products listed in Table 5 or 9. In another embodiment the method comprises determining the levels of all the gene products listed in Table 9 in the sample, to thereby obtain the urinary proteomic signature of the subject with respect to said gene products. Each possibility represents a separate embodiment of the invention.

In other embodiments of the methods of the invention, the subject is presented with at least two systemic inflammatory response syndrome (SIRS) criteria. In another embodiment, the subject is suspected of having sepsis. In another embodiment, the inflammation is acute. In another embodiment, the inflammation is chronic. In another embodiment, the subject is afflicted with an infection (e.g. bacterial or viral). In another embodiment, said subject is afflicted with a condition selected from the group consisting of an autoimmune disease, a rheumatic disease, a chronic inflammatory disease, and cancer. Each possibility represents a separate embodiment of the invention.

In another embodiment of the methods of the invention, determining the levels of said gene products is performed by an immunoassay. In various embodiments, the immunoassay is selected from the group consisting of dipstick, ELISA (including various multiplexed ELISA technologies), an antibody array, an antibody chip, a lateral flow test, and multiplex bead immunoassay. In another embodiment determining the levels of said gene products is performed by mass spectrometry or using a spectrophotometer.

In another embodiment of the methods of the invention, step b. is performed using a learning and pattern recognition algorithm. For example, the algorithm may include, without limitation, supervised classification algorithms including, but not limited to, gradient boosted trees, random forest, regularized regression, multiple linear regression (MLR), principal component regression (PCR), partial least squares (PLS), discriminant function analysis (DFA) including linear discriminant analysis (LDA), nearest neighbor, artificial neural networks, multi-layer perceptrons (MLP), generalized regression neural network (GRNN), and combinations thereof, or non-supervised clustering algorithms, including, but not limited to, K-means, spectral clustering, hierarchical clustering, gaussian mixture models, and combinations thereof. In a particular embodiment, the algorithm is selected from the group consisting of gradient boosted trees, random forest, regularized regression, and combinations thereof. In another embodiment, step b. is performed by computer-implemented methods, e.g. using a system providing for data analysis using an algorithm as disclosed herein.

In another embodiment of the methods of the invention, step b. comprises comparing the level of each gene product to a predetermined cutoff. In another embodiment, the control levels are determined from a urine sample of at least one subject diagnosed with the relevant condition (e.g. healthy subjects or subjects in a particular grade of inflammation), from a panel of control samples obtained from a set of subjects diagnosed with said condition, or from a stored set of data from subjects diagnosed with said condition.

Typically, the subject according to the methods of the invention is human. In another embodiment, said subject is at least two years of age. In another embodiment, said subject is an adult human.

In another aspect, the invention provides a method of detecting the presence or absence of severe systemic inflammation in a human subject of at least two years of age, comprising:

a. determining, in a urine sample of the subject, the levels of one or more gene products selected from the group consisting of: SAA1, SAA2 and GUCA2B gene products, and b. comparing the level of each gene product to the respective value corresponding to its urinary level in a healthy control subject, wherein significantly enhanced levels of the one or more gene products compared to their levels in a healthy control subject indicates that said subject has severe systemic inflammation.

In a particular embodiment, the gene product is SAA2. In a further particular embodiment, said gene product is a peptide having the amino acid sequence GNYDAAKRGPG-GAW (SEQ ID NO: 1). In another particular embodiment, the gene product is SAA1. In yet another particular embodiment, the gene product is GUCA2B. In another embodiment, significantly enhanced levels of the at least two gene products compared to their respective levels in a healthy control indicates that said subject has severe systemic inflammation. In another particular embodiment, said at least two gene products comprise SAA2. In another particular embodiment, the at least two gene products comprise SAA1. In another particular embodiment, the at least two gene products are SAA1 and SAA2. In yet another embodiment, significantly enhanced levels of SAA1, SAA2 and GUCA2B gene products (e.g. at least 30%-50% enhancement) compared to their respective levels in a healthy control indicates that said subject has severe systemic inflammation. Each possibility represents a separate embodiment of the invention.

In another embodiment, determining the levels of said gene products is performed by an immunoassay. In another embodiment the immunoassay is selected from the group consisting of dipstick, ELISA, an antibody array, an antibody chip, a lateral flow test, and a multiplex bead immunoassay. In another embodiment the subject is afflicted with an infection. In another embodiment the subject is afflicted with a condition selected from the group consisting of an autoimmune disease, a rheumatic disease, a chronic inflammatory disease, and cancer. In another embodiment, the method further comprises providing treatment to a subject detected as having severe systemic inflammation, wherein the treatment is selected from the group consisting of antibiotic drugs, anti-inflammatory drugs, immunosuppressants, and corticosteroids. In another embodiment said subject is an adult human.

As disclosed herein, methods according to embodiments of the invention provide for early treatment for an inflammatory condition, as correct diagnosis and treatment assignment can be made within hours from symptoms onset, without the need to wait for confirmatory test results. For example, a subject presented with signs or symptoms of systemic inflammation or a condition as disclosed herein may be tested with assays and methods according to embodiments of the invention that may advantageously provide a prompt answer (e.g. within minutes). Thus, correct treatment assignment may advantageously be provided early during the course of disease (e.g. within 1-4 hours or 1-24 hours of the onset of disease symptoms), before the disease progresses to a more severe and potentially life-threatening stage.

In another aspect, the invention provides an article of manufacture comprising means for specifically detecting and/or determining the levels of at least three gene products selected from the group consisting of the gene products listed in Tables 1 and 4-6, or from any one of Tables 9-14, in a urine sample. In one embodiment, the means comprise antibodies specific to the gene products. In another embodiment, said gene products are all the gene products as set forth in at least one of Tables 1, 4, 5, 6, and 9-14, wherein each possibility represents a separate embodiment of the invention. In a particular embodiment, said gene products are SAA2, SAA1, and GUCA2B gene products. In another particular embodiment, the means comprise an antibody directed to a peptide of SEQ ID NO: 1. In various embodiments, the article of manufacture is in the form of a dipstick, an antibody array, an antibody chip, a lateral flow test, or the like.

In another aspect there is provided a diagnostic kit, comprising the article of manufacture. In one embodiment, the means comprise antibodies specific to the gene products. In another embodiment the kit further comprises a container for collecting the urine sample. In another embodiment said kit further comprises means for comparing the level of each gene product in the sample to the respective value corresponding to its urinary level in a control sample. In another embodiment said kit further comprises instructions for use, for example instructions for comparing the level of each gene product to the respective value corresponding to its level in a control urine sample, to thereby compare the urinary proteomic signature of said subject to the urinary proteomic signature of the control sample and detect, evaluate or monitor systemic inflammation. In another embodiment, the kit further comprises reference controls. In another embodiment, the kit further comprises a suitable treatment, e.g. as described herein. In another embodiment the kit comprises antibodies directed to one or more gene products selected from the group consisting of: SAA2, SAA1, and GUCA2B. In another embodiment the kit comprises an antibody directed to a SAA2 gene product of SEQ ID NO: 1.

In another aspect there is provided an isolated peptide of the amino acid sequence GNYDAAKRGPGGAW (SEQ ID NO: 1). In another embodiment there is provided a conjugate comprising the isolated peptide and a heterologous moiety (e.g. carrier protein or label). In another embodiment there is provided a nucleic acid molecule encoding the isolated peptide. In another embodiment there is provided a method of producing an antibody directed to the peptide, comprising immunization with the peptide and isolation of the resulting antibody.

Other objects, features and advantages of the present invention will become clear from the following description and drawings.

BRIEF DESCRIPTION OF THE DRAWINGS

FIG. 1A—GUCA2B; FIG. 1B—SAA1; FIG. 1C—SAA2.

DETAILED DESCRIPTION OF THE INVENTION

Figure 1A:
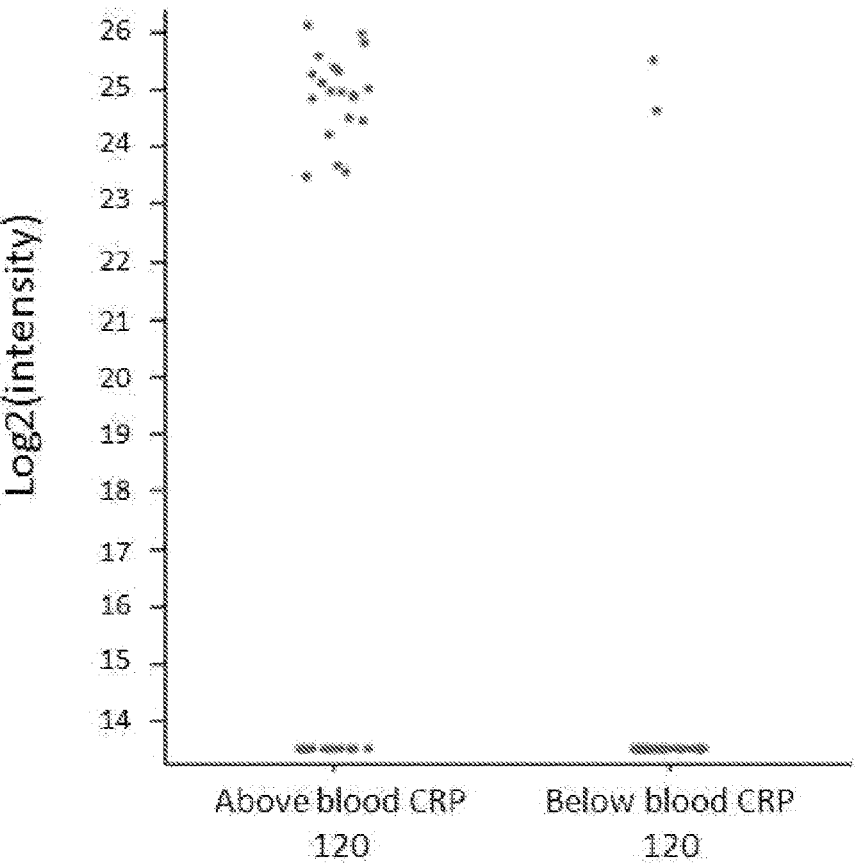
FIGS. 1A-1C. depict uniparametric analyses of urine proteins capable of identifying severe systemic inflammation characterized by blood CRP>120 mg/L. Results presented as base 2 logarithm of the urine levels measured in each subject (log 2(intensity)).

The invention provides assays, kits and methods for detecting and monitoring systemic inflammation. Particularly, the invention relates in some embodiments to the use of urinary biomarkers for non-invasive evaluation of the level of inflammation. The invention further relates in some embodiments to means for determining and adjusting treatment to a subject based on non-invasive assessment of the level and/or risk of developing inflammatory complications.

In one aspect, there is provided a method of detecting the presence or absence of systemic inflammation in a subject in need thereof, comprising:
 a. determining, in a urine sample from the subject, the levels of at least three gene products selected from the group consisting of the gene products listed in any one of Tables 6 and 10-14, to thereby obtain the urinary proteomic signature of the subject with respect to the at least three gene products, and
 b. comparing the level of each gene product to the respective value corresponding to its level in a reference control urine sample, to thereby obtain the urinary proteomic signature of said subject as compared to the urinary proteomic signature of the reference control sample.

In some embodiments, a method of detecting systemic inflammation in a subject in need thereof, comprises:
 a. obtaining a urine sample from the subject,
 b. determining the levels of at least three gene products selected from the group consisting of the gene products listed in any one of Tables 6 and 10-14 in the sample, to thereby determine the urinary proteomic signature of the subject with respect to the at least three gene products, and
 c. comparing the level of each gene product to the respective value corresponding to its level in a reference control urine sample, to thereby compare the urinary proteomic signature of said subject to the urinary proteomic signature of the reference control sample.

In one embodiment, the reference control sample corresponds to a healthy control subject, and a urinary proteomic signature substantially different from the urinary proteomic signature of the healthy control indicates that said subject has systemic inflammation. In another embodiment, the reference control sample corresponds to a healthy control subject, and a urinary proteomic signature characterized by significantly enhanced levels of said gene products compared to their levels in said control sample indicates that said subject has systemic inflammation.

In another embodiment, the method further comprises determining the level of systemic inflammation in said subject. In another embodiment, the inflammation is selected from the group consisting of mild, moderate and severe. In another embodiment, the reference control sample has been obtained from said subject at a time point preceding the time of obtaining the urine sample from said subject, and the method is further used for monitoring changes in the inflammatory state of said subject. In another embodiment the urine sample of the subject is a first urine sample obtained from said subject at a first time point, and the reference control sample is a second urine sample obtained from the same subject at a time point preceding the time of obtaining the first urine sample from said subject, wherein the method is used for monitoring changes in the inflammatory state of said subject. In another embodiment, a urinary proteomic signature characterized by significantly enhanced levels of the at least three gene products compared to their respective levels at the preceding time point is indicative of aggravation of systemic inflammation in said subject, and a urinary proteomic signature characterized by significantly reduced levels of the at least three gene products compared to their respective levels at the preceding time point is indicative of amelioration of systemic inflammation in said subject.

In another embodiment, the method further comprises adjusting treatment provided to said subject, wherein aggravation of systemic inflammation in said subject indicates that the treatment should be adjusted. In another embodiment, the method further comprises determining treatment for said subject based on the level of systemic inflammation determined. In another embodiment, the method further comprises providing said subject with the treatment. In another embodiment, said treatment is selected from the group consisting of antibiotic drugs, anti-inflammatory drugs, immunosuppressants, and corticosteroids.

In another embodiment, the method comprises determining the levels of at least five gene products selected from the group consisting of the gene products listed in Table 6 in the sample, to thereby determine the urinary proteomic signature of the subject with respect to the at least five gene products. In another embodiment, the method comprises determining the levels of all the gene products listed in Table 6 in the sample, to thereby determine the urinary proteomic signature of the subject with respect to said gene products. In another embodiment the method comprises determining the levels of at least five gene products selected from the group consisting of the gene products listed in any one of Tables 6 and 10-14 in the sample, to thereby obtain the urinary proteomic signature of the subject with respect to the at least five gene products. In another embodiment the at least three gene products are selected from the group consisting of the gene products listed in any one of Tables 10-14. In another embodiment the method comprises determining the levels of all the gene products listed in Table 10, in Table 11, in Table 12, in Table 13 or in Table 14, in the sample, to thereby determine the urinary proteomic signature of the subject with respect to said gene products. In another embodiment a urinary proteomic signature characterized by significantly enhanced levels of SAA1, SAA2 and GUCA2B gene products indicates that said subject has severe systemic inflammation.

In another embodiment, step b. is performed using a learning and pattern recognition algorithm. In another embodiment, said subject is human. In another embodiment, said subject is an adult human. In another embodiment, determining the levels of said gene products is performed by an immunoassay. In another embodiment, the immunoassay is selected from the group consisting of dipstick, ELISA, an antibody array, an antibody chip, a lateral flow test, and a multiplex bead immunoassay. In another embodiment, the subject is afflicted with an infection. In another embodiment, said subject is afflicted with a condition selected from the group consisting of an autoimmune disease, a rheumatic disease, a chronic inflammatory disease, and cancer. In another embodiment, the method further comprises providing disease prognosis for said subject. In another embodiment, the subject has received an immunostimulatory treatment, and the method is used for assessing the presence of, or the risk for developing, cytokine release syndrome (CRS). In another embodiment the subject has received an immunosuppressive treatment, and the method is used for determining treatment efficacy. In another embodiment the method comprises providing disease prognosis and/or corresponding treatment for said subject detected with said inflammation.

In another aspect, there is provided a method of detecting the presence or absence of severe systemic inflammation, comprising:

a. determining, in a urine sample of a subject, the levels of at least three gene products selected from the group consisting of the gene products listed in any one of Tables 4, 5 and 9, to thereby obtain the urinary proteomic signature of the subject with respect to the at least three gene products, and b. comparing the level of each gene product to the respective value corresponding to its urinary level in a healthy control subject, to thereby obtain the urinary proteomic signature of said subject as compared to the urinary proteomic signature of the healthy control subject.

In some embodiments, a method of detecting severe systemic inflammation comprises:

a. obtaining a urine sample from the subject, b. determining the levels of at least three gene products selected from the group consisting of the gene products listed in any one of Tables 4, 5 and 9 in the sample, to thereby determine the urinary proteomic signature of the subject with respect to the at least three gene products, and c. comparing the level of each gene product to the respective value corresponding to its urinary level in a healthy control subject, to thereby compare the urinary proteomic signature of said subject to the urinary proteomic signature of the healthy control subject.

In another embodiment, wherein a urinary proteomic signature substantially different from the urinary proteomic signature of the healthy control indicates that said subject has severe systemic inflammation. In another embodiment, a urinary proteomic signature characterized by significantly enhanced levels of said gene products compared to their levels in said control sample indicates that said subject has severe systemic inflammation. In another embodiment, said inflammation is associated with blood CRP levels >120 mg/L, and the gene products are selected from the group consisting of the gene products listed in Table 4. In a particular embodiment, the method comprises determining the levels of all the gene products listed in Table 4 in the sample, to thereby determine (or obtain) the urinary proteomic signature of the subject with respect to said gene products. In another embodiment, said inflammation is associated with blood CRP levels >100 mg/L, and the gene products are selected from the group consisting of the gene products listed in Table 5 or 9. In a particular embodiment, the method comprises determining the levels of all the gene products listed in Table 5 in the sample, to thereby determine (or obtain) the urinary proteomic signature of the subject with respect to said gene products. In another embodiment the method comprises determining the levels of all the gene products listed in Table 9 in the sample, to thereby obtain the urinary proteomic signature of the subject with respect to said gene products. In another embodiment the method comprises determining the levels of all the gene products listed in Table 5 in the sample, to thereby obtain the urinary proteomic signature of the subject with respect to said gene products.

In another embodiment, step b. is performed using a learning and pattern recognition algorithm. In another embodiment, said subject is human. In another embodiment, said subject is an adult human. In another embodiment, determining the levels of said gene products is performed by an immunoassay. In another embodiment, the immunoassay is selected from the group consisting of dipstick, ELISA, an antibody array, an antibody chip, a lateral flow test, and a multiplex bead immunoassay. In another embodiment, the subject is afflicted with an infection. In another embodiment, said subject is afflicted with a condition selected from the group consisting of an autoimmune disease, a rheumatic disease, a chronic inflammatory disease, and cancer. In another embodiment, the method further comprises providing disease prognosis for said subject. In another embodiment, the subject has received an immunostimulatory treatment, and the method is used for assessing the presence of, or the risk for developing, CRS. In another embodiment the subject has received an immunosuppressive treatment, and the method is used for determining treatment efficacy. In another embodiment the method comprises providing disease prognosis and/or corresponding treatment for said subject detected with said inflammation.

In another aspect, there is provided a method of detecting the presence or absence of severe systemic inflammation in a human subject of at least two years of age, comprising:

a. determining, in a urine sample of the subject, the levels of one or more gene products selected from the group consisting of: SAA2, SAA1, and GUCA2B gene products, and b. comparing the level of each gene product to the respective value corresponding to its urinary level in a healthy control subject, wherein significantly enhanced levels of the one or more gene products compared to their healthy control levels indicates that said subject has severe systemic inflammation.

In some embodiments, a method of detecting severe systemic inflammation in a human subject of at least two years of age comprises:

a. obtaining a urine sample from the subject, b. determining the levels of one or more gene products selected from the group consisting of: SAA1, SAA2 and GUCA2B gene products in the sample, and c. comparing the level of each gene product to the respective value corresponding to its urinary level in a healthy control subject, wherein significantly enhanced levels of the one or more gene products compared to their levels in a healthy control subject indicates that said subject has severe systemic inflammation.

In another embodiment, significantly enhanced levels of at least two gene products compared to their respective levels in a healthy control indicates that said subject has severe systemic inflammation. In another embodiment significantly enhanced levels of at least two gene products compared to their respective healthy control levels indicates that said subject has severe systemic inflammation. In another embodiment, the at least two gene products are SAA1 and SAA2. In another embodiment significantly enhanced levels of SAA1, SAA2 and GUCA2B gene products compared to their respective levels in a healthy control indicates that said subject has severe systemic inflammation. In another embodiment significantly enhanced levels of SAA1, SAA2 and GUCA2B gene products compared to their respective healthy control levels indicates that said subject has severe systemic inflammation. In another embodiment said gene product is a SAA2 gene product. In another embodiment said gene product is a peptide having the amino acid sequence GNYDAAKRGPGGAW (SEQ ID NO: 1). In another embodiment said gene product is a SAA1 gene product. In another embodiment said gene product is a GUCA2B gene product. In another embodiment, enhancement of at least 50% in the level of said marker (e.g. SAA1) in said sample compared to its level in a healthy control subject indicates that said subject has severe systemic inflammation. In another embodiment determining the levels of said gene products is performed by an immunoassay. In another embodiment the immunoassay is selected from the group consisting of dipstick, ELISA, an antibody array, an antibody chip, a lateral flow test, and a multiplex bead immunoassay. In another embodiment the subject is afflicted with an infection or with a condition selected from the group consisting of an autoimmune disease, a rheumatic disease, a chronic inflammatory disease, and cancer. In another embodiment, the method further comprises providing disease prognosis for said subject. In another embodiment said subject is an adult human. In another embodiment the method further comprises providing treatment to a subject detected as having severe systemic inflammation, wherein the treatment is selected from the group consisting of antibiotic drugs, anti-inflammatory drugs, immunosuppressants, and corticosteroids.

In another aspect, there is provided a method for analyzing a urine sample, comprising:

a. determining the levels of at least three gene products selected from Table 1 in the sample, to thereby obtain the urinary proteomic signature of the sample with respect to the at least three gene products, and b. comparing the level of each gene product to the respective value corresponding to its urinary level in a reference control urine sample, to thereby obtain the urinary proteomic signature of said sample as compared to the urinary proteomic signature of the control sample.

In one embodiment, step b. is performed using a learning and pattern recognition algorithm. In another embodiment, said subject is human. In another embodiment, said subject is an adult human. In another embodiment determining the levels of said gene products is performed by an immunoassay. In another embodiment the immunoassay is selected from the group consisting of dipstick, ELISA, an antibody array, an antibody chip, a lateral flow test, and a multiplex bead immunoassay. In another embodiment the subject is afflicted with an infection or with a condition selected from the group consisting of an autoimmune disease, a rheumatic disease, a chronic inflammatory disease, and cancer. In another embodiment, the method further comprises providing disease prognosis and/or corresponding treatment for said subject detected with said inflammation.

In another aspect, the invention provides an article of manufacture comprising means for specifically detecting and determining the levels of at least three gene products selected from the group consisting of the gene products listed in Tables 1 and 4-6 or from any one of Tables 9-14, in a urine sample. In another embodiment said gene products are all the gene products as set forth in at least one of Tables 1, 4, 5 and 6. In another embodiment said gene products are all the gene products as set forth in at least one of Tables 9-14. In another embodiment, said article of manufacture is in the form of a dipstick, an antibody array, an antibody chip, or a lateral flow test.

In another embodiment, there is provided a diagnostic kit, comprising the article of manufacture. In another aspect, there is provided a diagnostic kit, comprising means for specifically detecting and determining the levels of at least three gene products selected from the group consisting of the gene products listed in Tables 1 and 4-6, or from any one of Tables 9-14, in a urine sample. In another embodiment, the means comprise antibodies specific to the gene products. In another embodiment, said gene products are all the gene products as set forth in at least one of Tables 1, 4, 5 and 6 or in at least one of Tables 9-14. Each possibility represents a separate embodiment of the invention.

In another embodiment the kit further comprises a container for collecting the urine sample and/or means for comparing the level of each gene product in the sample to the respective value corresponding to its urinary level in a healthy control subject. In another embodiment the gene products comprise one or more gene products selected from the group consisting of: SAA2, SAA1, and GUCA2B. In another embodiment the kit comprises an antibody directed to a SAA2 gene product of SEQ ID NO: 1.

In another aspect, there is provided an isolated peptide of the amino acid sequence GNYDAAKRGPGGAW (SEQ ID NO: 1). In another embodiment there is provided a conjugate comprising the isolated peptide and a heterologous moiety. In another embodiment there is provided a nucleic acid molecule encoding the isolated peptide. In another embodiment there is provided a method of producing an antibody directed to the peptide, comprising immunization with the peptide and isolation of the resulting antibody.

Subjects and Samples

According to various embodiments of the methods and assays of the invention, a urine sample is obtained from a subject. The subject according to the methods of the invention is typically a human subject. According to some embodiments, the subject is at least two years of age, or in other embodiments an adult human subject.

According to embodiments of the invention, the methods and assays as disclosed herein may be used for detecting, quantifying or monitoring systemic inflammation in subjects diagnosed or afflicted with various conditions that may be associated with inflammation. In one embodiment, the subject is afflicted with an infection. In other embodiments, the subject may be afflicted with a non-infective inflammatory condition. For example, the subject may be afflicted with (or suspected of having) an autoimmune disease, a rheumatic disease, or a chronic inflammatory disease. In another embodiment the subject is afflicted with cancer.

In various embodiments, the infection may be a bacterial, viral or parasitic, wherein each possibility represents a separate embodiment of the invention. For example, without limitation, the subject may be afflicted with a bacterial or viral infection selected from the group consisting of Epstein-Barr virus (EBV) infection, cytomegalovirus (CMV) infection, measles, parainfluenza bronchitis, upper respiratory tract infection (URTI), lower respiratory tract infection, rash, varicella-zoster virus (VZV) infection, sternitis, peritonitis, pneumonia, *Rickettsia* infection, cellulitis, folliculitis, diverticulitis, colitis, dental infection, bacterial endocarditis, myositis, bacteremia, ascending cholangitis, abscess (e.g. abdominal, liver, lung or perianal abscess), bacterial pharyngitis, cholecystitis, (e.g. gangrenous cholecystitis), empyema, osteomyelitis, parotitis, viral infections associated with asthma exacerbation, bronchitis, dengue infection, herpes zoster infection, infectious mononucleosis, influenza, meningitis, and combinations thereof. In other exemplary embodiments, the subject may be afflicted with a bacterial or viral infection selected from the group consisting of EBV infection, CMV infection, measles, parainfluenza bronchitis, URTI, lower respiratory tract infection, rash, VZV infection, sternitis, peritonitis, pneumonia, *rickettsia* infection, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. Each possibility represents a separate embodiment of the invention. Thus, the level of inflammation, rather than the etiology of the infection, is determined by methods according to the invention. In yet other embodiments, the subject is not afflicted with an infection as disclosed herein.

In another embodiment the condition is an autoimmune disease, in which the subject's immune system attacks the subject's own tissue. Exemplary autoimmune diseases include but are not limited to multiple sclerosis, rheumatoid arthritis, systemic lupus erythematosus (SLE), myasthenia gravis, and inflammatory bowel disease (Crohn's and ulcerative colitis). These conditions are typically mediated by an auto-immune inflammatory response characterized by the presence of host-specific antibodies and/or T cells, which correlates with the disease severity.

In another embodiment the conditions include rheumatic diseases, which are inflammatory joint diseases. Inflammatory joint diseases refer to damage or partial or complete destruction to any part of one or more joints, including the connective tissue and cartilage, where damage includes structural and/or functional damage of any cause and is characterized by inflammation in the joint, and may or may not cause joint pain (arthralgia). In one example, the inflammatory joint damage is caused by arthritis, such as, rheumatoid arthritis, osteoarthritis, ankylosing spondylitis, or psoriatic arthritis.

In another embodiment, said disorder is a chronic inflammatory disease. A chronic inflammatory disease is characterized by a persistent inflammatory response with pathologic sequelae. This state is typically accompanied by infiltration of mononuclear cells, proliferation of fibroblasts and small blood vessels, increased connective tissue, and tissue destruction. Non-limitative examples include idiopathic or non-infective chronic conditions, e.g. pericarditis or periodontitis.

In other embodiments the condition is a neoplastic disorder (cancer). In various embodiments, the cancer is selected from glioma, leukemia, uterine cancer, lymphoma, neuroblastomas, pancreatic cancer, prostate cancer, clear cell renal carcinoma, colorectal, lung, and breast tumors, and melanoma. In such conditions, the subject may be prone to developing infections due to chemotherapy, irradiation or other immune-suppressive treatments or to manifest inflammatory symptoms due to other immune-modulating treatments. For example, immunotherapy (e.g. by CAR T cells) or immunostimulatory treatments may be associated with the development of cytokine release syndrome (CRS).

In some embodiments, the subject is not afflicted with renal injury or disease, e.g. chronic kidney disease. In some embodiments the subject is not afflicted with (or has not been diagnosed as having) urinary tract infection. In other embodiments, the subject is not presented with leukocyturia. In other embodiment the subject is not presented with renal or genitourinary symptoms or signs. In other embodiments the subject is not presented with impaired glomerular filtration or progressive deterioration of glomerular filtration. In other particular embodiments, the subject is not diagnosed with, or suspected of having, tuberculosis or necrotizing enterocolitis. In another particular embodiment, the subject is not diagnosed with, or suspected of having, COVID-19. In yet another embodiment, said subject is afflicted with, or suspected of having, COVID-19. Each possibility represents a separate embodiment of the invention.

The urine sample to be used in embodiments of the invention is obtained or collected from the subject as is known in the art. Typically, the urine sample is obtained non-invasively, as disclosed herein. In one embodiment, the urine sample is a voided urine sample. In a particular embodiment the sample is collected from the subject without a preceding step of bladder scraping or washing. In another embodiment, the method further comprises the step of freezing the urine sample obtained and thawing the sample prior to the step of determining the levels of gene products. Conveniently, urine samples may be kept at −20° C. or −80° C. until the analysis is performed. Yet in other embodiments the invention relates to rapid diagnostic and prognostic methods, in which the sample is assayed within hours (e.g. 1-4 hours or less than 24 hours) or minutes (e.g. up to 15, 30 or 45 minutes) of collection. In one embodiment, the sample is a non-sedimented urine sample. In another embodiment, the urine sample is substantially free of residual cells. Each possibility represents a separate embodiment of the invention.

In various embodiments, the methods of the present invention further comprise diluting the urine sample before determining the level of the marker(s). In one embodiment, the sample is diluted in the range of 1:2 to 1:20 for instance, using PBS. In another embodiment, the sample is diluted 1:4, 1:6, 1:8, 1:10, 1:15 or 1:20, e.g. prior to subjecting the sample to an immunoassay. In another embodiment, the urine sample undergoes concentration or filtration. In a preferable embodiment, the sample undergoes ultra-filtration using, for instance, a MILLIPORE Amicon Ultra. As is known in the art, ultra-filtration relates to a variety of membrane filtration in which hydrostatic pressure forces a liquid against a semipermeable membrane. The cut-off of the membrane may be selected from 3 KD, 10 KD, 30 KD or more. In another embodiment, the sample is reconstituted (e.g. with PBS). In another embodiment, following reconstitution, the urine sample is diluted in the range of times 2-times 10 (e.g. prior to subjecting the sample to an immunoassay). In yet other exemplary embodiments (e.g. for analysis using mass spectrometry), the samples may be concentrated by filtration (e.g. using 3 kDa molecular weight cutoff filters) and then subjected to in-solution tryptic digestion, followed by a desalting step. Each possibility represents a separate embodiment of the invention.

Assays and Kits

According to various embodiments, the methods and assays of the invention involve determining the levels of gene products as disclosed herein in urine samples.

In certain embodiments, methods of the invention are performed by an immunoassay, using antibodies specific to gene products of the invention.

An antibody directed (or specific) to an antigen, as used herein is an antibody which is capable of specifically binding the antigen. The term "specifically bind" as used herein means that the binding of an antibody to an antigen probe is not competitively inhibited by the presence of non-related molecules.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; recombinant and engineered antibodies, and fragments thereof.

Exemplary functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens.

In some embodiments, determining the levels of gene products of the invention in the sample is performed by a process comprising contacting the sample, under conditions such that a specific antigen-antibody complex may be formed, with antibodies directed to the gene products of interest, and quantifying the amount of antigen-antibody complex formed for each gene product, to thereby determine (or obtain) the urinary proteomic signature of the subject with respect to said gene products.

In various embodiments, the immunoassay is selected from the group consisting of dipstick, ELISA (including various multiplexed ELISA technologies), an antibody array, an antibody chip, a lateral flow test, and multiplex bead immunoassay.

In accordance with the principles of the invention, any suitable immunoassay can be used. Such techniques are well known to the ordinarily skilled artisan and have been described in many standard immunology manuals and texts. In certain embodiments, determining the capacity of the antibodies to specifically bind the gene products is performed using an antibody array-based method, including, but not limited to an antibody array or an antibody chip. In some embodiments, the array is incubated with an optionally diluted urine sample of the subject so as to allow specific binding between the gene products contained in the sample and the immobilized antibodies, washing out unbound components from the array, incubating the washed array with detectable label-conjugated antibodies of the desired isotype, washing out unbound label from the array, and measuring levels of the label bound to each gene product.

Additional exemplary assays may be based on dipstick technology, as demonstrated, for example, in U.S. Pat. Nos. 4,632,901, 4,313,734 and 4,786,589 5,656,448 and EP 0125118. For example, U.S. Pat. No. 4,632,901, discloses a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample. EP 0125118 discloses a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

In certain embodiments, the detection of the biomarkers (gene products) may be performed using other immunoassays such as an enzyme-linked immunosorbent assay (ELISA) testing kit. In such assays, for example, samples are typically incubated in the presence of an immobilized first specific binding agent (e.g. an antibody) capable of specifically binding the biomarker. Binding of the biomarker to said first specific binding agent may be measured using any one of a variety of known methods, such as using a labeled second specific binding agent capable of specifically binding the biomarker (at a different epitope) or the first specific binding agent. Exemplary specific binding agents include e.g. monoclonal antibodies, polyclonal antibodies, and antibody fragments such as recombinant antibody fragments, single-chain antibodies (scFv) and the like. In some embodiments, various conventional tags or labels may be used, such as a radioisotope, an enzyme, a chromophore or a fluorophore. A typical radioisotope is iodine$^{-125}$ or sulfur$^{-35}$. Typical enzymes for this purpose include horseradish peroxidase, horseradish galactosidase and alkaline phosphatase.

Alternately, other immunoassays may be used; such techniques are well known to the ordinarily skilled artisan and have been described in many standard immunology manuals and texts. In some embodiments, the methods of the invention are suitable for automated or semi-automated analysis, and may enable clinical, medium or high-throughput screening of multiple samples. For example, automated ELISA systems such as Biotest's Quickstep® ELISA Processor, Maxmat Automated microwell ELISA analyzer (Maxmat S. A., France), or DSX™ Four-Plate System (Dynex Technologies) may conveniently be used, and employed in various methods including, but not limited to multiplexed ELISA methods. Other suitable assays include for example flow cytometry assays (such as singleplex and multiplex bead-based Luminex® assays (Invitrogen), or other multiplex bead immunoassays available in the art.

Lateral flow tests operate on the same principles as ELISA assays as described above. In essence, these tests run the sample along the surface of a pad with reactive molecules that show a visual positive or negative result. The pads are based on a series of capillary beds, such as pieces of porous paper, microstructured polymer, or sintered polymer. Each of these pads has the capacity to transport fluid (e.g., urine) spontaneously. The sample pad acts as a sponge and holds an excess of sample fluid. Once soaked, the fluid flows to the second conjugate pad in which freeze dried bio-active particles called conjugates are stored in a salt-sugar matrix. The conjugate pad contains all the reagents required for an optimized chemical reaction between the target molecule (e.g., a gene product as disclosed herein) and its chemical partner (e.g., antibody) that has been immobilized on the particle's surface. This marks target particles as they pass through the pad and continue across to the test and control lines. The test line shows a signal, often a color. The control line contains affinity ligands which show whether the sample has flowed through and the bio-molecules in the conjugate pad are active. After passing these reaction zones, the fluid enters the final porous material, the wick, that acts as a waste container.

In another embodiment determining the levels of said gene products is performed by mass spectrometry or using a micro-spectrometer. For example, mass spectrometry-based, targeted proteomics may be employed, e.g. using heavy labeled synthetic internal standards for the proteolytic peptides of said gene products. The native peptides and the standards may be measured using a mass spectrometer and the signal from the internal standard is referenced to the native peptides, which represent the original gene products in the urine sample. In a non-limitative example, suitable equipment such as the SCIO Near Infrared mini Spectrometer may be used.

Additional embodiments of the invention are directed to articles of manufacture comprising means for specifically detecting and/or determining the levels of gene products as disclosed herein in urine samples. In various embodiments, said article of manufacture comprises means for specifically detecting and determining the levels of a gene product set as disclosed herein. In some embodiments, the means comprise, consists of, or essentially include, antibodies specific to the gene products of a gene product set as disclosed herein. In some embodiments, the article of manufacture is configured in the form of an immunoassay as disclosed herein, including, but not limited to a dipstick, an antibody array, an antibody chip, or a lateral flow test. In other embodiments, said article of manufacture is amenable for use with an immunoassay as disclosed herein, including, but not limited to a dipstick, an antibody array, an antibody chip, or a lateral flow test.

According to further aspects, the present invention provides kits suitable for use in the methods of the invention. In some embodiments, there is provided a diagnostic kit comprising the article of manufacture. In some embodiments, the kit may further comprise a suitable container or other means for collecting the urine sample. In other embodiments the kit further comprises means for comparing the level of each gene product in the sample to the respective value corresponding to its urinary level in a control sample. In some embodiments, there is provided a diagnostic kit comprising i) means for collecting a urine sample from a subject and ii) means for determining the level of gene products of the invention in the sample.

In other embodiments, the kit may further contain additional means for determining the level of gene products, including, but not limited to reagents, detectable labels and/or containers which may be used for measuring specific binding of antibodies to the marker antigens of the invention. In other embodiments, the kit may further comprise means for comparing a urinary proteomic signature to control proteomic signatures. In some embodiments the kit contains negative and/or positive control samples. For example, control samples may contain a sample from at least one healthy individual. In other embodiments, the control samples may include a panel of control samples from a set of healthy individuals or diseased individuals as disclosed herein, or a stored set of data corresponding to control individuals. Optionally, the kits may further comprise means for preparing or processing the sample before measuring the marker levels. In various embodiments, the control samples correspond to subjects diagnosed with systemic inflammation, e.g. severe systemic inflammation as described herein. In an exemplary embodiment, a gene product (e.g. peptide)

as disclosed herein may be included in the kit, as a positive control to validate the sensitivity and specificity of the assay. Each possibility represents a separate embodiment of the invention.

In further embodiments the kits further comprise instructions for use, e.g. for using said kits in a diagnostic or analytical method as disclosed herein. In other embodiments, the kit further comprises instructions for assigning treatment or treating a subject according to the methods as disclosed herein. In some embodiments, the kit further comprises a treatment for use on the diagnosed subject, for example corticosteroids or other anti-inflammatory or immune-suppressive drugs. Each possibility represents a separate embodiment of the invention.

In various embodiments, the invention relates to combinations of gene products, also referred to herein as marker sets or subsets, which are detected or quantified in urine samples. In some embodiments, a urinary proteomic signature is determined with respect to a marker set as disclosed herein. In various embodiments, the marker sets include the gene products listed in Table 1 herein, or a subset thereof as disclosed herein. In various embodiments, the marker sets include at least 3 gene products, e.g. 4, 5, 6, 7, 8, 9, 10, 11, 12, 13, 15 or in other embodiments up to about 9, 10, 12, 13, 15 or 20 gene products of those listed in Table 1 herein. as exemplified herein, the marker set may include 3-15 gene products, e.g. 3-5 (Tables 4, 9, 12, 14 and Examples 1 and 3), 5-10 (Tables 4, 5, 12, 14 and Examples 1 and 3), or 10-15 (Tables 5, 6, 10, 11, Examples 1-3) gene products, wherein each possibility represents a separate embodiment of the invention. In some embodiments, the gene products include, or are selected from the group consisting of, those set forth in Table 4, 5, 6, 9, 10, 11, 12, 13 or 14, or include SAA1, SAA2 and GUCA2B gene products. Each possibility represents a separate embodiment of the invention.

In a particular embodiment, the gene products include an SAA gene product, e.g. an SAA2 gene product. In another particular embodiment, the SAA2 gene product is an SAA2 peptide or fragment as disclosed herein. in yet another embodiment, said gene products do not include an SAA2 gene product. Each possibility represents a separate embodiment of the invention.

In some embodiments, the gene products do not include tumor necrosis factor-related apoptosis-inducing ligand (TRAIL) and/or CXCL10 (IP-10) gene products. In another embodiment said gene product does not include C-reactive protein (CRP). In other embodiments, the gene products do not include human neutrophil lipocalin (HNL), sCD14-ST (soluble CD14 antigen subtype; presepsin), urinary trypsin inhibitor (uTi), and/or neopterin. Each possibility represents a separate embodiment of the invention.

In another embodiment, the markers (gene products) used in connection with the articles of manufacture, kits and assays of the invention comprise, consist of or essentially include a marker set as disclosed herein. Each possibility represents a separate embodiment of the invention.

Diagnostic Applications

According to various embodiments of the methods and assays of the invention, the level of each gene product is compared to the respective value corresponding to a control urine sample. In some embodiments, the control urine sample corresponds to a healthy control subject. In other embodiments, the control urine sample corresponds to a sample obtained from said subject at a time point preceding the time of obtaining the urine sample from said subject (and may be used for example for monitoring changes in the inflammatory state of said subject). In other embodiments (for example in methods for determining the level of systemic inflammation), the control urine sample corresponds to a subject with a predetermined level of inflammation. Such control samples are also referred to herein collectively as reference control samples.

In one embodiment, the methods of the invention are used for the assessment of systemic inflammation in a subject in need thereof, including detecting (diagnosing), determining the level of (grading or quantifying), and monitoring changes in the inflammatory state (comparing the level of systemic inflammation in a patient to its level at a previous time point).

In one embodiment, the methods of the invention are used for (or comprise) detecting systemic inflammation in a subject in need thereof. As used herein, the term "systemic inflammation" refers to an immune-mediated inflammatory state affecting multiple portions or organs of the body. In contradistinction, local inflammation is confined to a particular location or organ. A systemic inflammation may be an infective inflammation (e.g. when the subject is afflicted with an infection as disclosed herein) or a sterile inflammation (sterile systemic inflammation, e.g. when the subject is afflicted with a non-infective inflammatory condition such as an autoimmune disease, a rheumatic disease, or other types of chronic inflammatory diseases).

Non-limiting examples of symptoms of systemic inflammation include: altered body temperature (e.g., less than 36° C. or greater than 38° C.), increased heart rate (e.g., greater than 90 beats per minute), tachypnea (e.g., greater than 20 breaths per minute), decreased arterial pressure of $CO_2$ (e.g., less than 4.3 kPa), altered white blood count (e.g., less than 4,000 cells/mm$^3$ or greater than 12,000 cells/mm$^3$), increased histamine levels (e.g., greater than 60 ng/mL in blood), increased leukotriene B4 levels (e.g., greater than 30 pg/mL or greater than 35 pg/mL in blood), increased prostaglandin levels (e.g., greater than 3.0 ng/mL in blood), increased levels of pro-inflammatory cytokines (e.g., greater than 20 ng/mL TNF-α and/or greater than 10 pg/mL IL-6).

In another embodiment the method is used for (or comprises) determining the level of systemic inflammation in a subject in need thereof. In various embodiments the inflammation is selected from the group consisting of mild (low-grade or chronic), moderate and severe. Acute systemic inflammation is typically either moderate (intermediate grade) or severe (high grade, typically spread to more organs and systems). One type of high-grade systemic inflammation is systemic inflammatory response syndrome (SIRS). Manifestations of SIRS include abnormally high or low body temperature, elevated heart rate, high respiratory rate, and abnormal white blood cell counts. Generally, SIRS is defined as a condition in which at least two of the following criteria (hereinafter "SIRS criteria") are met: fever >38° C. or <36° C.; heart rate >90 beats per minute; respiratory rate >20 breaths per minute or PaCO$_2$<32 mm Hg; and abnormal white blood cell count (>12,000/mm$^3$ or <4,000/mm$^3$ or >10% bands).

Systemic inflammation is traditionally evaluated by measuring blood markers such as erythrocyte sedimentation rate (ESR) and CRP, wherein elevated CRP levels indicate a more severe grade of inflammation. For example, the level of systemic inflammation may be determined as being mild, moderate or severe, characterized by blood CRP levels of 10-39, 40-100, or over 100 mg/L, respectively. In contradistinction, healthy subjects (or subjects in which inflammation is inhibited by suitable treatment), are characterized by blood CRP levels of up to 10 mg/L, although some individual subjects may manifest blood CRP levels of up to 30 mg/L without significant clinical manifestation. In a particular embodiment the method is used for (or comprises) detecting severe systemic inflammation (e.g. characterized by blood CRP levels over 100 mg/L or 120 mg/L).

In some embodiments, the control urine sample corresponds to a subject with a predetermined level of inflammation (e.g. mild, moderate or severe as disclosed herein), and determining the level of systemic inflammation comprises comparing the level of each gene product to the respective value corresponding to its level in one or more such reference samples, or to predetermined cutoffs differentiating between the urinary level of said gene product in a healthy control subject and a subject with systemic inflammation, and/or between the predetermined levels of systemic inflammation.

In another embodiment the method is used for (or comprises) monitoring changes in the inflammatory state of a subject in need thereof (e.g. when the reference control sample has been obtained from said subject at a time point preceding the time of obtaining the urine sample from said subject). Thus, aggravation (enhancement) or amelioration (reduction) of systemic inflammation (e.g. correlated with significantly enhanced or significantly reduced blood CRP levels, respectively), may be determined. In some embodiments, aggravation or amelioration in the inflammatory state of a subject will typically result in aggravation or amelioration, respectively, of one or more symptoms of systemic inflammation as disclosed herein. The methods and assays of embodiments of the invention provide for prompt assessment of the inflammatory state, thereby predicting alterations in the level of inflammation even before alterations in the symptoms may be observed clinically.

In another embodiment the method is used for (or comprises) providing disease prognosis for said subject. According to exemplary embodiments, high-grade inflammation or aggravation in the inflammatory state may be indicative of poor prognosis, while mild or no infection, or amelioration of the inflammatory state, may indicate a favorable disease condition or prognosis.

In another embodiment the method is used for (or comprises) assessing the presence of, or the risk for developing, cytokine release syndrome (CRS). CRS is a form of systemic inflammatory response syndrome (SIRS) that can be triggered by a variety of factors such as infections and certain drugs. CRS occurs when large numbers of white blood cells are activated and release inflammatory cytokines, which in turn activate yet more white blood cells. When occurring as a result of a therapy (e.g. certain monoclonal antibody medications, adoptive T-cell therapies or other immunostimulatory treatments), CRS symptoms may be delayed until days or weeks after treatment. Immediate-onset CRS and severe cases of CRS may also be referred to as a cytokine storm (CSS). According to exemplary embodiments, high-grade inflammation or aggravation in the inflammatory state may be indicative of the presence or risk of CRS.

In another embodiment, the method is used for (or comprises) determining treatment efficacy, as will be described in further detail below. In another exemplary embodiment, the method is used for (or comprises) early detection of inflammation associated with an infection, e.g. in cancer patients undergoing irradiation or chemotherapy.

In other embodiments, the methods of the invention are used for non-invasively prognosing, evaluating disease progression of, determining and/or adjusting treatment for, a subject afflicted with a condition associated with elevated blood CRP levels In another aspect, there is provided a method of non-invasively monitoring the progression of a condition associated with elevated blood CRP levels in a subject in need thereof. Each possibility represents a separate embodiment of the invention.

In some embodiments, a urinary proteomic signature substantially different from the urinary proteomic signature of the healthy control indicates that said subject has systemic inflammation. In other embodiments a urinary proteomic signature substantially different from the urinary proteomic signature of the healthy control indicates that said subject has severe systemic inflammation.

In other embodiments, a urinary proteomic signature characterized by significantly enhanced levels of gene products compared to their levels in said control sample indicates that said subject has systemic inflammation. In another embodiment a urinary proteomic signature characterized by significantly enhanced levels of gene products compared to their levels in said control sample indicates that said subject has severe systemic inflammation.

In another embodiment a urinary proteomic signature characterized by significantly enhanced levels of the at least three gene products compared to their respective levels at the preceding time point is indicative of aggravation of systemic inflammation in said subject, and a urinary proteomic signature characterized by significantly reduced levels of the at least three gene products compared to their respective levels at the preceding time point is indicative of amelioration of systemic inflammation in said subject. In another embodiment significantly enhanced levels of the one or more gene products as disclosed herein compared to their levels in a healthy control subject indicates that said subject has severe systemic inflammation.

In some embodiments of the methods of detecting, determining the level of, and monitoring systemic inflammation, the gene products may be selected from the group consisting of the gene products listed in any one of Tables 6 and 10-14, wherein Each possibility represents a separate embodiment of the invention. In another embodiment the determining step comprises determining the levels of at least five gene products selected from the group consisting of the gene products listed in any one of Tables 6 and 10-14 in the sample, to thereby obtain the urinary proteomic signature of the subject with respect to the at least five gene products, wherein each possibility represents a separate embodiment of the invention. In another embodiment, the determining step comprises determining the levels of the gene products listed in Table 6 in the sample, to thereby obtain the urinary proteomic signature of the subject with respect to said gene products. In another embodiment the determining step comprises determining the levels of the gene products listed in Table 10, in Table 11, in Table 12, in Table 13 or in Table 14, in the sample, to thereby obtain the urinary proteomic signature of the subject with respect to said gene products, wherein each possibility represents a separate embodiment of the invention.

In another embodiment, as demonstrated herein, the gene products listed in Tables 11 and 12 are particularly suitable for detecting and determining the level of inflammation in subjects in which blood CRP levels are higher than 30 mg/L, and are thus particularly useful in connection with moderate and severe systemic inflammation. In a particular embodiment, the gene products include, or are selected from, LRG1, UMOD, DDT; DDTL, and FCN2 gene products.

In another embodiment, as demonstrated herein, the gene products of Tables 13 and 14 enable accurate identification of the inflammatory state based on their presence or absence in the urine samples, and do not require exact quantification of their levels. Accordingly, these gene products are particularly useful in connection with immunoassays intended for self-diagnosis by the patient, such as dipstick assays. In a particular embodiment, the gene products include, or are selected from, MATN4, LGALS1, CRHBP, and DLK1 gene products.

In some embodiments of the methods of detecting severe systemic inflammation, the gene products are selected from the group consisting of the gene products listed in any one of Tables 4, 5 and 9, wherein each possibility represents a separate embodiment of the invention. In other embodiments of the methods of detecting severe systemic inflammation, the gene products include one or more gene products selected from the group consisting of: SAA1, SAA2 and GUCA2B gene products. In other embodiments of the methods of detecting severe systemic inflammation, the gene products include one or more gene products selected from the group consisting of: SRGN, ASGR1 and IGLV3-12 gene products.

In another embodiment said inflammation is associated with blood CRP levels >120 mg/L, and the gene products are selected from the group consisting of the gene products listed in Table 4. In another embodiment the determining step comprises determining the levels of the gene products listed in Table 4 in the sample, to thereby determine the urinary proteomic signature of the subject with respect to said gene products. In another embodiment said inflammation is associated with blood CRP levels >100 mg/L, and the gene products are selected from the group consisting of the gene products listed in Table 5 or 9, wherein each possibility represents a separate embodiment of the invention. In another embodiment the determining step comprises determining the levels of the gene products listed in Table 5 in the sample, to thereby determine the urinary proteomic signature of the subject with respect to said gene products. In another embodiment the determining step comprises determining the levels of the gene products listed in Table 9 in the sample, to thereby determine the urinary proteomic signature of the subject with respect to said gene products. In another embodiment the determining step comprises determining the levels of one or more gene products listed in Table 9 in the sample, wherein significantly enhanced levels of the one or more gene products indicates that said subject has severe systemic inflammation. In another embodiment significantly enhanced levels of the one or more gene products selected from the group consisting of: SAA1, SAA2 and GUCA2B gene products compared to their levels in a healthy control subject indicates that said subject has severe systemic inflammation, wherein each possibility represents a separate embodiment of the invention.

According to embodiments of the invention, substantial difference or similarity of proteomic signatures are determined considering the collective levels of gene products of the signature. In some embodiments, a substantially different urinary proteomic signature compared to a control comprises significantly enhanced levels of a set of gene products as disclosed herein compared to their respective control levels. In other embodiments a substantially different urinary proteomic signature compared to a control comprises significantly reduced levels of a set of gene products as disclosed herein compared to their respective control levels. In yet other embodiments, a substantially different urinary proteomic signature compared to a control comprises both significantly enhanced levels of one or more markers as disclosed herein and significantly reduced levels of one or more additional markers as disclosed herein compared to their respective control levels. Each possibility represents a separate embodiment of the invention. As used herein, "significant enhanced" and "significantly reduced" levels refer to statistically significant enhancement/reduction, respectively.

In some embodiments, comparing proteomic signatures can be performed using suitable classifiers or algorithms, including, but not limited to, learning and pattern recognition algorithms, supervised classifiers, and the like. A significant difference from control levels, may typically and conveniently be performed considering the respective values of both negative and positive control groups (e.g. healthy control subjects and subjects afflicted with systemic inflammation, respectively). The methods according to embodiments of the invention may include a step of determining the respective level of gene products as disclosed herein in positive and/or negative control samples, or may employ comparison of the values measured in the test sample to the respective predetermined values or stored data. The test sample may thereby be classified as corresponding to (substantially similar to, or not substantially different from) either the positive or negative control group, as disclosed herein. The positive and negative controls referred to herein typically and conveniently represent control sets, such as a panel of control samples from a set of healthy or similarly-diagnosed individuals, or a stored set of data obtained from healthy or similarly-diagnosed individuals.

Thus, in some embodiments of the methods of the invention, the comparing step is performed using a learning and pattern recognition algorithm as disclosed herein. In a particular embodiment, the algorithm is selected from the group consisting of gradient boosted trees, random forest, regularized regression, and combinations thereof, wherein each possibility represents a separate embodiment of the invention.

In another embodiment of the methods of the invention, the comparing step comprises comparing the level of each gene product to a predetermined cutoff differentiating between the urinary level of said gene product in a healthy control subject and a subject with systemic inflammation (or between predetermined levels of systemic inflammation).

In some embodiments, the determining and comparing steps comprise determining the presence or absence of each marker in the sample, wherein the urinary proteomic signature reflects said presence or absence of each marker in said sample. According to additional embodiments, comparing the urinary protein signatures further includes comparing the level of each gene product (including the presence or absence of said gene product) to its control urinary level in a specific order or hierarchy, to thereby compare the urinary proteomic signature of said subject to the control urinary proteomic signature. For instance, Example 3 herein demonstrates comparison of urinary proteomic signature using decision tree algorithms, in which the presence or absence of the markers (SRGN, IGLV3-12, and ASGR1) is considered in a specific hierarchy.

In various embodiments, the invention relates to methods useful in evaluation of inflammation in cases in which existing assays are lacking, lengthy or otherwise inappropriate or inadvisable. The invention in embodiments thereof overcomes these and other challenges as disclosed herein by assaying a urine sample of said subject in a prompt and non-invasive manner. In some embodiments, the methods of the invention for early treatment for infectious disease, as correct diagnosis and treatment assignment (in particular of antibiotic treatment) can be made within hours (e.g. 1-4 hours or less than 24 hours) from symptoms onset. In some embodiments of the methods of the invention, the determining and comparing steps are performed within 15 minutes, 30 minutes, 60 minutes, 1-4 hours, 3-6 hours or up to 24 hours, collectively, wherein each possibility represents a separate embodiment of the invention.

Treatment Assessment and Assignment

In some embodiments, the methods of the invention provide for treatment assignment methods and therapeutic methods, comprising e.g. adjusting, determining and/or providing treatment, wherein each possibility represents a separate embodiment of the invention. In various embodiments of the treatment assignment methods, the subject may be afflicted with an infective or non-infective inflammatory condition as disclosed herein. Accordingly, the treatment to be adjusted, determined and/or provided to the subject is a treatment for the corresponding condition (including for the associated inflammatory response).

In one embodiment, the methods of the invention comprise adjusting treatment provided to the subject (e.g. a drug or agent as disclosed herein). In another embodiment, aggravation of systemic inflammation in the subject indicates that the treatment should be adjusted. Adjusting the treatment may include in some embodiments replacing the treatment, providing an additional treatment, and/or altering (typically enhancing) the administered dose or duration of said treatment, such that the adjusted treatment corresponds to a more severe form or grade of the disease.

In another embodiment the methods of the invention comprise determining (selecting) treatment for a subject based on the level of systemic inflammation determined in the subject. For example, without limitation, determining treatment may comprise determining a suitable dose, wherein e.g. higher doses are used in severe inflammation compared to moderate inflammation, and the dosage may further be reduced for cases of or mild inflammation. In another non-limitative example, more potent immunosuppressive drugs are used in severe cases compared to less severe cases. Exemplary doses and drugs with various potencies are provided hereinbelow.

In another embodiment the methods of the invention further comprise providing said subject with the treatment. Accordingly, in some embodiments there is provided a method of treating a subject in need thereof, comprising:

a. obtaining a urine sample from the subject, b. determining the levels of at least three gene products selected from the group consisting of the gene products listed in any one of Tables 6 and 10-14 in the sample, to thereby determine the urinary proteomic signature of the subject with respect to the at least three gene products, and c. comparing the level of each gene product to the respective value corresponding to its level in a reference control urine sample, to thereby compare the urinary proteomic signature of said subject to the urinary proteomic signature of the reference control sample, d. determining the level of systemic inflammation in said subject (e.g. as mild, moderate or severe), e. determining treatment for said subject based on the level of systemic inflammation determined, and f. providing said subject with the treatment.

In various embodiments, the treatment to be adjusted, determined and/or provided in the methods of the invention (e.g. in the case of non-infective inflammatory conditions) may be anti-inflammatory drugs, immunosuppressants, or corticosteroids. For example, anti-inflammatory drugs include, without limitation, non-steroidal anti-inflammatory drugs NSAID) and anti-cytokine agents such as anti-IL6 mAb (e.g. Actemra), anti-IL-1 mAb (e.g. Anakinra) and anti-TNF mAb (e.g. Remicade); immunosuppressants or immunosuppressive agents have negative immunoregulatory activities and include e.g. cyclosporine and methotrexate. Corticosteroids have both anti-inflammatory and immunoregulatory activity and include e.g. prednisone, dexamethasone, and hydrocortisone.

Thus, in an exemplary embodiment (e.g. in the treatment of IBD or similar conditions), corticosteroids or other potent treatments may be provided to a subject determined to have severe systemic inflammation, less potent immunosuppressants may be provided to a subject with moderate systemic inflammation, and mild anti-inflammatory drugs such as NSAID may be provided to subjects with mild inflammation, or in combination with other treatments in moderate and severe cases.

In another embodiment the treatment may be an antibiotic drug (e.g. when the presence or level of inflammation in infective conditions is determined). For example, the antibiotic treatment may include e.g. broad-spectrum gram-positive antibiotics, broad-spectrum gram-negative antibiotics, and combinations thereof. For example, broad-spectrum gram-positive antibiotics may include, without limitation, vancomycin or linezolid. Broad-spectrum gram-negative antibiotics may include, without limitation, broad-spectrum penicillins such as piperacillin and tazobactam, $3^{rd}$- or $4^{th}$-generation cephalosporins, imipenems, and aminoglycoside. In yet another embodiment, the treatment excludes an antibiotic drug.

Doses and treatment regimens for disease-specific treatments e.g. as listed above are known in the art and may be determined and adjusted by the skilled artisan (e.g. treating physician) according to the patient's characteristics and disease manifestations.

For example, NSAIDs inhibit the generation of prostaglandins by blocking cyclooxygenase enzymes, COX-1 and COX-2. The major effect of these agents is to reduce acute inflammation thereby decreasing pain and improving function. All of these drugs also have mild to moderate analgesic properties independent of their anti-inflammatory effect. There are a large number of NSAIDs, some over the counter including ibuprofen and naproxen and many others are available by prescription including meloxicam, etodolac, nabumetone, sulindac, tolementin, choline magnesium salicylate, diclofenac, diflusinal, indomethacin), ketoprofen, meloxicam, oxaprozin, and piroxicam. Longer acting NSAIDs that allow daily or twice daily dosing may improve compliance. The NSAID class also includes drugs known as COX-2 inhibitors that are also effective in controlling inflammation, e.g. celecoxib, etoricoxib, and lumiracoxib. NSAID doses for the treatment of various autoimmune and inflammatory conditions are known in the art. For example, for the treatment of SLE, ibuprofen may be used as needed or in doses up to 3000 mg a day, and naproxen is typically used as 500 mg twice a day.

Corticosteroids (including, but not limited to prednisone; methylprednisolone) have both anti-inflammatory and immunoregulatory activity. They can be given orally, intravenously, intramuscularly or can be injected directly into the joint. In mild SLE, for example, prednisolone is given in doses starting at 0.1-0.3 mg/kg/day followed by a gradual tapering dose regimen according to clinical response. The dose rises to 0.4-0.6 mg/kg/day in moderate disease and as high as 0.7-1.5 mg/kg/day in very severe disease. At such high doses, pulse therapy with intravenous (IV) methylprednisolone (MP; 500-1000 mg on one to three occasions) is deemed by many physicians to be safer with fewer associated side effects. IV therapy is considered in patients that have not responded to oral therapy and/or have serious manifestations of SLE such as lupus nephritis, neuropsychiatric disease, severe refractory thrombocytopenia, hemolytic anemia, severe vasculitis and cardiopulmonary disease.

Azathioprine is an immunosuppressive agent commonly used for the induction of remission and as a steroid-sparing agent in mild-to-moderate autoimmune diseases. It works by affecting cell-mediated and humoral immune responses via the inhibition of lymphocyte proliferation, reduction in antibody production and suppression of natural killer cell activity. In severe disease, it is used as maintenance therapy and data from lupus nephritis trials show significant improvement in disease activity following induction therapy with cyclophosphamide or mycophenolate mofetil.

Other biological agents and immunosuppressive agents include for example monoclonal antibodies targeting several surface molecules on B cells, to reduce the formation of auto-antibodies. Such exemplary drugs include rituximab (anti-CD20), ocrelizumab (humanized anti-CD20), belimumab (anti-BAFF/BLyS), atacicept (anti-BLys/APRIL) and epratuzumab (humanized anti-CD22). In addition, other key cell-surface markers have been developed to interfere with costimulatory molecules such as cytotoxic T lymphocyte antigen 4 (abatacept). In addition, Leflunomide (original brand name Arava) is an immunosuppressive pyrimidine synthesis inhibitor that works by inhibiting dihydroorotate dehydrogenase. Leflunomide is an immunomodulatory drug that inhibits the reproduction of rapidly dividing cells, especially lymphocytes. In addition, TNF-α inhibitors, e.g. Etanercept or Infliximab, may be used in some cases.

In other embodiments, the methods of the invention may be used for evaluating the subject's response to various treatments, e.g. immunostimulatory treatment or immunosuppressive treatment.

In some embodiments, the methods are used for evaluating adverse effects associated with immunostimulatory treatment. Such treatments include various cancer immunotherapies including, but not limited to, CAR T cells and adoptive transfer cell therapy, and checkpoint inhibitors (e.g. PD-1 and PDL-1 inhibitors). In an exemplary embodiment, the subject has received an immunostimulatory treatment, and the method is used for assessing the presence of, or the risk for developing, cytokine release syndrome (CRS).

In other embodiments, the methods of the invention are used for evaluating the therapeutic effects of immunosuppressive treatments e.g. one or more drugs or agents as disclosed herein exhibiting negative immune regulatory effects. In some embodiments the subject has received an immunosuppressive treatment, and the method is used for determining treatment efficacy (e.g. inhibition of inflammation or autoimmunity manifested as reduction in the inflammatory state as disclosed herein).

SAA Gene Products

Serum amyloid A (SAA) proteins are a family of apolipoproteins associated with high-density lipoprotein (HDL) in plasma, comprising different constitutively expressed and inducible isoforms. These proteins are produced predominantly by the liver. SAA1 and SAA2, listed in Tables 1 and 4-6 herein, are highly homologous. As disclosed herein, SAA1 and SAA2 are particularly useful prognostic markers, which may be used in various embodiment of the invention as described in further detail herein.

As is further disclosed herein, the gene products of the invention may be found in human urine samples in the form of fragments or peptides, rather than as intact polypeptides.

Accordingly, urine-borne gene products as disclosed herein may differ structurally from the corresponding gene products that may be found in blood or bodily tissues, as lacking portions of the corresponding native polypeptides. It is to be understood, that the term "gene product" as referred to herein explicitly includes these partial fragments and peptides e.g. C-terminally truncated and/or N-terminally truncated fragments. As further disclosed herein, these peptides may include in particular N-terminally truncated fragments of SAA gene products. In other embodiments, the gene products referred to herein are intact (or substantially intact) polypeptides.

For example, it was unexpectedly found that both SAA1 and SAA2 are present in the urine samples during inflammation as endogenous peptides, as described in Example 5 herein. In particular, the SAA2-derived peptide, GNYDAAKRGPGGAW (SEQ ID NO: 1), exhibited remarkable correlation (0.78) with blood CRP levels, and found particularly useful as a marker for inflammation.

Accordingly, another aspect of the invention relates to an isolated peptide having the amino acid sequence of SEQ ID NO: 1.

The peptides of the invention may be isolated or synthesized using any recombinant or synthetic method known in the art, including, but not limited to, solid phase (e.g. Boc or f-Moc chemistry) and solution phase synthesis methods. For example, the peptides can be synthesized by a solid phase peptide synthesis method of Merrifield (1963 J. Amer. Chem. Soc. 85:2149-2156). Alternatively, a peptide of the present invention can be synthesized using standard solution methods well known in the art (see, for example, Bodanszky, 1984 The Principles of Peptide Synthesis, Springer-Verlag, New York) or by any other method known in the art for peptide synthesis.

In alternate embodiments, the peptides may be produced by recombinant technology. Recombinant methods for designing, expressing and purifying proteins and peptides are known in the art (see, e.g. Sambrook et al., Molecular Cloning: A Laboratory Manual, Cold Springs Harbor Laboratory, New York, 2001). Nucleic acid molecules according to the invention may include DNA, RNA, or derivatives of either DNA or RNA. An isolated nucleic acid sequence encoding a peptide can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional peptide of the present invention. A polynucleotide or oligonucleotide sequence can be deduced from the genetic code of a protein, however, the degeneracy of the code must be taken into account, as well as the allowance of exceptions to classical base pairing in the third position of the codon, as given by the so-called "Wobble rules". Moreover, polynucleotides that include more or less nucleotides can result in the same or equivalent proteins. Thus, according to other embodiments, the invention provides nucleic acids encoding the peptides of the invention, as well as recombinant constructs, expression vectors and pharmaceutical compositions thereof as known in the art (see, e.g. Sambrook et al., 2001).

In the methods of the invention, the term "peptide" relates to a sequence of 7-40 preferably 10-20 contiguous amino acids, linked by peptide bonds. The peptide may include both "L" and "D" amino acids as well as non-natural and chemically derivatized amino acids known in the art. Preferably, the peptides of the invention are 12-18 amino acids (aa) in length, more preferably about 14 aa in length.

As used herein, the term "isolated peptide" refers to either a synthetic peptide or a peptide which has been "altered by the hand of man" and separated from the co-existing materials of its natural state. An isolated peptide has been synthetically produced or changed or removed from its original environment and typically both.

Whenever peptides are mentioned in the invention, also salts and functional derivatives thereof are contemplated, as long as they retain the corresponding immune reactivity. Thus, the present invention encompasses peptides containing non-natural amino acid derivatives or non-protein side chains. The peptides of the invention may be used having a terminal carboxy acid, as a carboxy amide, as a reduced terminal alcohol or as any pharmaceutically acceptable salt, e.g., as metal salt, including sodium, potassium, lithium or calcium salt, or as a salt with an organic base, or as a salt with a mineral acid, including sulfuric acid, hydrochloric acid or phosphoric acid, or with an organic acid e.g., acetic acid or maleic acid.

The amino acid residues described herein are preferred to be in the "L" isomeric form. However, residues in the "D" isomeric form can be substituted for L-amino acid residues, as long as the peptide substantially retains the desired functional property (e.g. immune reactivity). The N' and C' of the peptides may optionally be derivatized by stabilizing chemical groups as known in the art, which do not substantially affect the structure or conformation of the peptide, such as by amidation, acetylation, conjugation of fatty acids and the like.

Further encompassed by embodiments of the invention are analog peptides obtained by replacement, deletion or addition of amino acid residues to the sequence, optionally including the use of a chemically derivatized residue in place of a non-derivatized residue. These analogs may be considered equivalent to the peptide corresponding to SEQ ID NO: 1 as long as they retain high sequence homology (at least 70% and typically 80%, 90% or more) and retain the corresponding immune reactivity (i.e. are cross-reactive with an antibody directed to SEQ ID NO: 1 under physiological conditions).

In some embodiments, the kits and assays of the invention advantageously incorporate the use of an antibody directed to an SAA2 fragment as disclosed herein.

In other embodiments there is provided a method of producing an antibody directed to the SAA fragments of the invention, comprising immunizing a subject (e.g. a non-human animal) with the peptide. The peptide may be used for immunization in the form of an immunogenic conjugate in which the isolated peptide is linked (e.g. by direct covalent bond or via a linker) to a heterologous sequence such as a carrier protein.

In other embodiments the invention relates to a conjugate of the isolated peptide with a heterologous moiety, e.g. a carrier or a label. In some embodiments, the conjugate may also be provided in the form of a multimeric conjugate comprising multiple copies of the peptide linked directly or via a linker. The antibody may then be isolated e.g. obtained directly from the sera of the immunized animals or further isolated by methods known in the art.

In another aspect the invention relates to an antibody, or an antigen-binding portion thereof, specific to the peptide of SEQ ID NO: 1. In various embodiments, the antibody is a monoclonal antibody, a polyclonal antibody, or a fragment thereof, as described herein. In another embodiment the antibody has been produced by a method comprising immunization with the peptide and isolation of the resulting antibody.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique.

In cases where target antigens are too small to elicit an adequate immunogenic response when generating antibodies in vivo, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). The antisera obtained can be used directly (e.g. as diluted sera or as purified polyclonal antibodies), or monoclonal antibodies may be obtained, as described herein.

A monoclonal antibody (mAb) is a substantially homogeneous population of antibodies to a specific antigen. The term "monoclonal antibody" as used herein refers to an antibody (typically intact) obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. mAbs may be obtained by methods known to those skilled in the art. For example, the monoclonal antibodies to be used in accordance with the present invention may be made by hybridoma methods, or may be made by recombinant DNA methods (see, e.g., U.S. Pat. No. 4,816,567). The "monoclonal antibodies" may also be isolated from phage antibody libraries. See, for example U.S. Pat. No. 4,376,110; Ausubel et al ("Current Protocols in Molecular Biology," Volumes I-III, John Wiley & Sons, Baltimore, Maryland, 1994).

Antibody fragments may be obtained using methods well known in the art. (See, for example, Harlow, E. and Lane, D. (1988). Antibodies: A Laboratory Manual, Cold Spring Harbor Laboratory, New York). For example, antibody fragments according to the present invention can be prepared by proteolytic hydrolysis of the antibody or by expression in *E. coli* or mammalian cells (e.g., Chinese hamster ovary (CHO) cell culture or other protein expression systems) of DNA encoding the fragment.

Besides the conventional method of raising antibodies in vivo, antibodies can be generated in vitro using phage display technology. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

In another aspect there is provided a method of analyzing a urine sample of a subject, comprising determining the level of an SAA2 gene product in the sample, and comparing said level to the respective value corresponding to its urinary level in a healthy control subject, or to a control sample obtained from said subject at a time point preceding the time of obtaining the urine sample from said subject. In a particular embodiment said gene product has the amino acid sequence of SEQ ID NO: 1. In another embodiment, the method further comprises determining the level of at least one additional gene product in said sample, e.g. one or more gene products as set forth in Table 1, 4, 5 or 6 (e.g. SAA1 and GUCA2B) and comparing their levels to the respective level in said control sample.

In another aspect there is provided a method for detecting systemic inflammation in a subject in need thereof, comprising:

a. obtaining a urine sample from the subject, b. determining the level of an SAA2 gene product in the sample, and c. comparing said level to the respective value corresponding to its urinary level in a healthy control subject, wherein a significantly enhanced level of the one or more gene products compared to their levels in a healthy control subject indicates that said subject has severe systemic inflammation. In a particular embodiment said gene product has the amino acid sequence of SEQ ID NO: 1. In another embodiment, the method further comprises determining the level of at least one additional gene product in said sample, e.g. one or more gene products as set forth in Table 1, 4, 5 or 6 (e.g. SAA1 and/or GUCA2B), and comparing their levels to the respective level in said control sample.

Data Analysis

In some embodiments, the methods of the invention can employ the use of learning and pattern recognition analyzers, clustering algorithms and the like, in order to discriminate between the proteomic signature of a sample or subject and control proteomic signatures as disclosed herein. For example, the methods can comprise determining the levels of at least three gene products as disclosed herein in a urine sample, and comparing the resulting urinary proteomic signature to the urinary proteomic signature of a healthy control using such algorithms and/or analyzers.

In certain embodiments, one or more algorithms or computer programs may be used for comparing the amount of each gene product quantified in the urine sample against a predetermined cutoff (or against a number of predetermined cutoffs). Alternatively, one or more instructions for manually performing the necessary steps by a human can be provided.

Algorithms for determining and comparing urinary proteomic signatures include, but are not limited to, supervised classification algorithms including, but not limited to, gradient boosted trees, random forest, regularized regression, multiple linear regression (MLR), principal component regression (PCR), partial least squares (PLS), discriminant function analysis (DFA) including linear discriminant analysis (LDA), nearest neighbor, artificial neural networks, multi-layer perceptrons (MLP), generalized regression neural network (GRNN), and combinations thereof, or nonsupervised clustering algorithms, including, but not limited to, K-means, spectral clustering, hierarchical clustering, gaussian mixture models, and combinations thereof. In a particular embodiment, the algorithm is selected from the group consisting of gradient boosted trees, random forest, regularized regression, and combinations thereof.

Many of the algorithms are neural network-based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

The following examples are presented in order to more fully illustrate some embodiments of the invention. They should, in no way be construed, however, as limiting the broad scope of the invention.

EXAMPLES

Example 1. Urinary Biomarkers for Detecting Severe Systemic Inflammation

A. Patients and Methods

Patient Characteristics

The study included a total of 76 adult participants, including 56 patients with acute infection, and 20 healthy volunteers as the control group. Of the infected patients, 25 were diagnosed with a bacterial infection, 9 patients had confirmed viral diagnosis, 7 were labeled as indeterminate etiology, and 15 were excluded). Exclusion criteria included leukocyturia (n=7), diagnosis of urinary tract infection (UTI; n=2), a-febrile patients (n=3) and patients with non-infectious etiology (n=3).

Patients diagnosed with bacterial infection were older and had a higher frequency of dyslipidemia compared to viral patients and controls. The patient cohort was balanced with respect to gender, BMI and prior diagnosis of hypertension.

The patient characteristics are summarized it Table 2 below. The infection etiologies and clinical diagnoses of the patients are listed in Table 3 below, along with a summary of tests by which the diagnoses were confirmed.

TABLE 2

Summary of patient characteristics

| Group | Bacterial infection | Viral infection | Control | p value |
|---|---|---|---|---|
| Patients (n) | 25 | 9 | 20 | |
| Age, years | 66.9 (17.0) | 43.6 (23.7) | 35.3 (9.5) | <0.001 |
| Gender, % male | 60% | 77.8% | 70.0% | 0.577 |
| BMI, kg/m$^2$ | 23.9 (3.2) | 24.7 (3.7) | 22.5 (2.1) | 0.400 |
| Hypertension, % | 56.0% | 33.3% | 0% | <0.001 |
| Dyslipidemia, % | 48.0% | 11.1% | 5% | 0.003 |

TABLE 3

Patient diagnoses

| | Bacterial infection | | Viral infection |
|---|---|---|---|
| Count | Diagnosis/Positive test | Count | Diagnosis/Positive test |
| 1 | Ascending cholangitis | 3 | Viral EBV/CMV |
| 1 | Abdominal bacterial infections | 2 | CMV |
| 1 | CT + ERCP + Clinical Dx | 2 | Positive Serology |
| 1 | Bacteremia | 1 | CMV IgM positive |
| 1 | Complicated bacterial infections | 1 | CMV IgM positive with conversion |
| 1 | Blood culture | 1 | EBV |
| 1 | Bacteremia + Myositis | 1 | Positive Serology |
| 1 | Complicated bacterial infections | 1 | EBV IgM + IgG |
| 1 | Blood culture | 2 | Viral Measles |
| 1 | Bacterial endocarditis | 2 | Measles |
| 1 | Complicated bacterial infections | 2 | Serology with seroconversion |
| 1 | Blood culture + Vegetation | 1 | Measles with seroconversion |
| 2 | Cellulitis | 1 | Measles with seroconversion + Urine PCR |
| 2 | Complicated bacterial infections | 3 | Viral Upper Respiratory Tract Infection (URTI)/Lower Respiratory Tract Infection (LTRI)/RASH |
| 2 | Clinical diagnosis | 1 | m/p Viral infection |
| 1 | Dental infection | 1 | Clinical diagnosis |
| 1 | Complicated bacterial infections | 1 | negative for measles |
| 1 | History + Dental procedure | 1 | m/p Viral URTI |
| 1 | Diverticulitis/Colitis | 1 | Clinical diagnosis |
| 1 | Abdominal bacterial infections | 1 | Parainfluenza bronchitis |
| 1 | Clinical diagnosis + CT | 1 | PCR |
| 1 | Deep Vein Thrombosis (DVT) + Cellulitis | 1 | Parainfluenza type 3 |
| 1 | Complicated bacterial infections | 1 | Viral VZV |
| 1 | History + US Doppler | 1 | VZV (V1) |
| 1 | Insect Bite + Cellulitis/folliculitis | 1 | PCR |
| 1 | Complicated bacterial infections | 1 | VZV positive (smear) |
| 1 | History | 9 | Total |
| 1 | Lung Abscess | | |
| 1 | Complicated bacterial infections | | |
| 1 | Chest CT + history | | |
| 1 | m/p Rickettsia | | |
| 1 | Community bacterial infections | | |
| 1 | Clinical diagnosis | | |
| 1 | m/p Bacterial infection | | |
| 1 | Abdominal bacterial infections | | |
| 1 | Clinical diagnosis | | |
| 1 | Perianal abscess | | |
| 1 | Abdominal bacterial infections | | |

TABLE 3-continued

| Patient diagnoses | | | |
| --- | --- | --- | --- |
| Bacterial infection | | Viral infection | |
| Count | Diagnosis/Positive test | Count | Diagnosis/Positive test |
| 1 | CT + Surgery | | |
| 7 | Pneumonia | | |
| 7 | Community bacterial infections | | |
| 1 | Clinical diagnosis + CT | | |
| 5 | Clinical diagnosis + CXR | | |
| 1 | CT + Clinical diagnosis | | |
| 1 | Pneumonia (atypical) | | |
| 1 | Community bacterial infections | | |
| 1 | History + CXR | | |
| 1 | Pneumonia with Emphyema | | |
| 1 | Community bacterial infections | | |
| 1 | Pleurocentesis culture | | |
| 1 | Spontaneous bacterial peritonitis (SBP) | | |
| 1 | Complicated bacterial infections | | |
| 1 | Clinical diagnosis + paracentesis | | |
| 1 | Sternitis | | |
| 1 | Complicated bacterial infections | | |
| 1 | Blood culture | | |
| 25 | Total | | |

Sample Preparation

Blood and urine were collected from patients upon hospitalization. Routine chemistry was analyzed immediately, and aliquots of serum and urine were frozen in −80° c. For proteomics analysis, the samples were concentrated using 3 kDa molecular weight cutoff filters and then subjected to in-solution tryptic digestion, followed by a desalting step.

Liquid Chromatography Mass Spectrometry (LC-MS)

The resulting peptides were analyzed using nanoflow liquid chromatography (nanoAcquity) coupled to high resolution, high mass accuracy mass spectrometry (Fusion Lumos). Each sample was analyzed separately in a random order in a discovery mode.

Data Processing

Raw data was processed with MaxQuant v1.6.6.0. The data were searched with the *Andromeda* search engine against the human proteome database appended with common lab protein contaminants. Quantification was based on the label-free quantification (LFQ) method, based on unique peptides.

Differential Expression analysis was calculated using limma software package. Missing values were treated based on the majority rules. If one of three replicates was zero, it was treated as Na (i.e. not included in the statistics), if two of three replicates were zero, it was changed to a constant low value (i.e. included in the statistics). False discovery rate (padj) was performed using Benjamini and Hochberg (BH). Significance was based on +/−2-fold change and p.adj<0.05.

Wide-Range C-Reactive Protein (wrCRP) measurements were done by ADVIA® Siemens Healthcare Diagnostics Inc., Tarrytown, NY 10591-5097 USA. The ADVIA® Chemistry wrCRP method measures CRP in serum and plasma by a latex-enhanced immunoturbidimetric assay.

B. Results

Proteomic analysis was performed on urine samples of 54 human subjects including subjects diagnosed with bacterial or viral infection, and infection-free subjects (listed in Table 3). Overall, 1307 proteins were detected in the urine samples. Following adjustment for age and gender, patients in the infection groups (bacterial and viral) were found to differ from the healthy control group in the urinary levels of 170 proteins. Blood CRP levels were further measured, and used as a reference biomarker to evaluate the level of systemic inflammation.

Figure 1B:
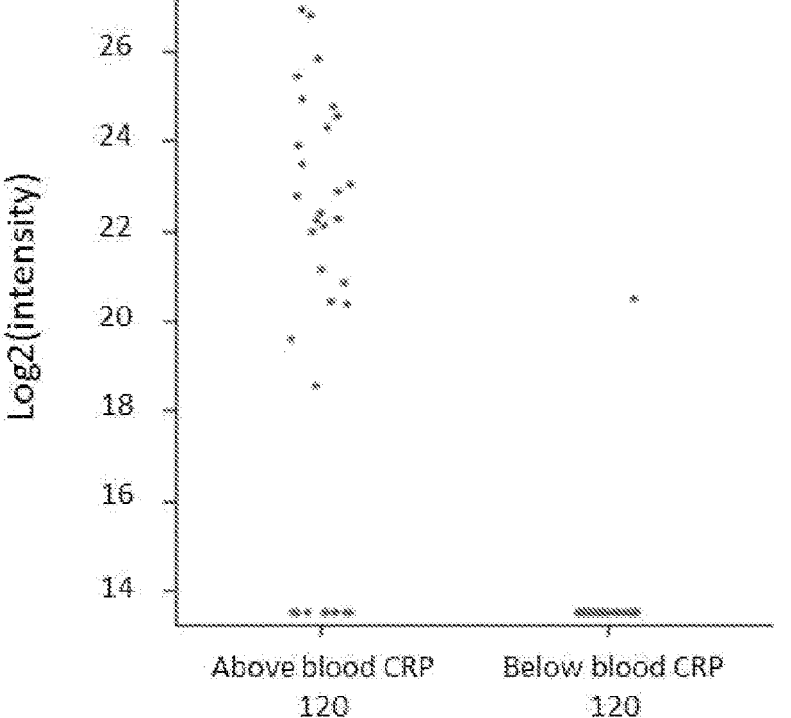
Figure 1C:
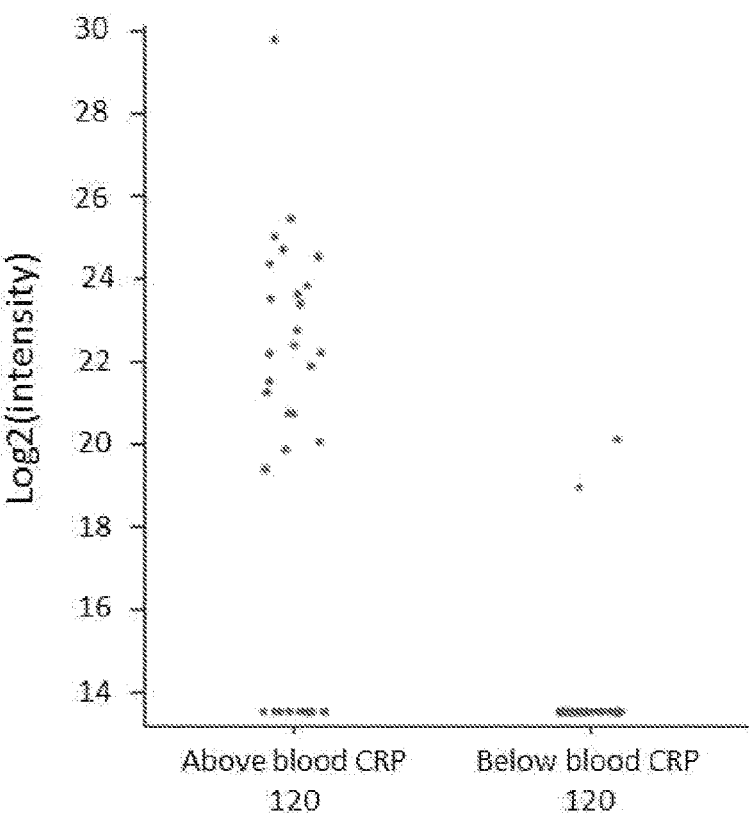

Surprisingly, three proteins were identified that were able to discriminate between patients with severe (and potentially life threatening) systemic inflammation characterized by blood CRP>120 mg/L, and the remaining subjects. FIGS. 1A-1C show the distribution of the urine levels of these proteins, namely Guanylate cyclase activator 2B, Serum amyloid A-1 and Serum amyloid A-2, respectively, in the two groups (uniparametric analyses, presented as base 2 logarithm). Further, multi-parameter analysis, using Linear Regression with L1 regularization using the R package glmnet was performed, with the regularization parameter chosen to minimize prediction error in a 10-fold cross validation. The analysis revealed that a combination of these three proteins recognized about 75% of the severe systemic inflammation cases.

Multi-parameter analysis using the XGBOOST algorithm was performed to identify additional combinations of urine proteins that differentiate well between subjects with severe systemic inflammation and subjects with non-severe or no inflammation. The analysis was done using the R package xgboost, with trees of depth 2, and a leave-one-out cross validation to assess the out of sample prediction error.

Figure 2:
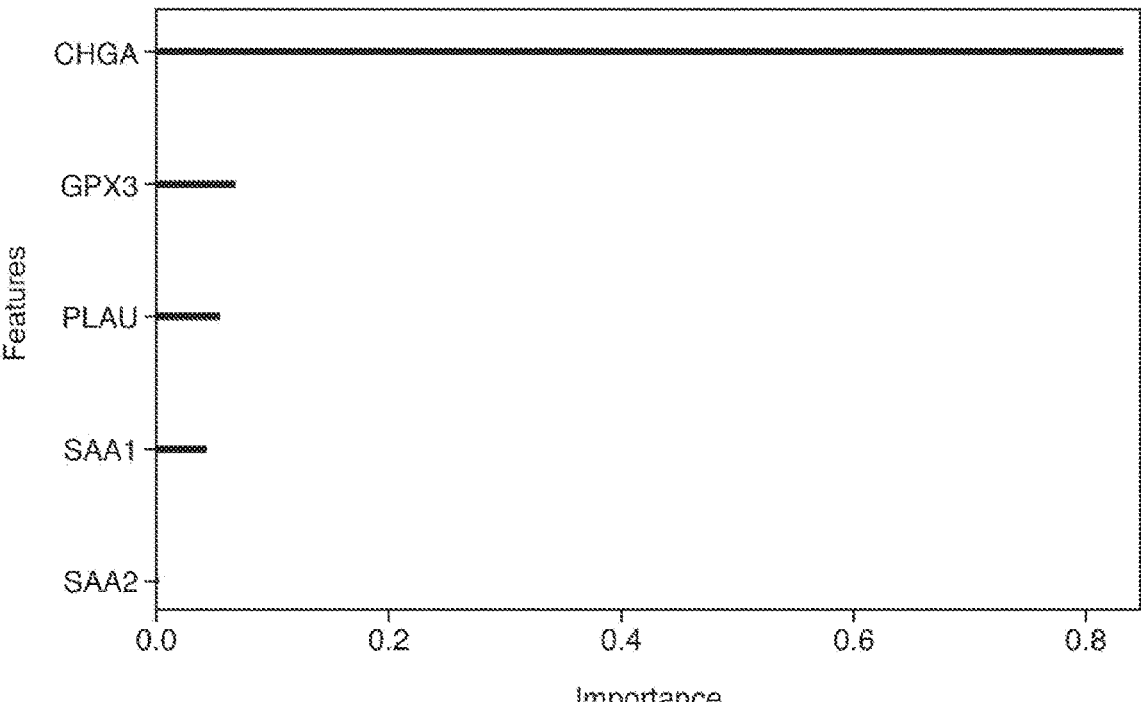
FIG. 2. shows a multi-parameter analysis using the XGBOOST algorithm, that can identify severe systemic inflammation characterized by blood CRP>120 mg/L. The relative importance of each of the urinary biomarkers in the model is indicated.

The analysis revealed a protein signature capable of identifying severe systemic inflammation characterized by blood CRP>120 mg/L with improved accuracy. The details of these proteins are provided in Table 4. FIG. 2 shows the relative importance of each of the urinary biomarkers in the model.

TABLE 4

| markers for severe systemic inflammation (blood CRP >120 mg/L) | | |
|---|---|---|
| Accession No. | Gene | Gene product |
| P10645 | CHGA | Chromogranin-A; Vasostatin-1; Vasostatin-2; EA-92; ES-43; Pancreastatin; SS-18; WA-8; WE-14; LF-19; Catestatin; AL-11; GV-19; GR-44; ER-37; GE-25; Serpinin-RRG; Serpinin; p-Glu serpinin precursor |
| P22352 | GPX3 | Glutathione peroxidase 3 |
| P00749 | PLAU | Urokinase-type plasminogen activator; Urokinase-type plasminogen activator long chain A; Urokinase-type plasminogen activator short chain A; Urokinase-type plasminogen activator chain B |
| P0DJI8 | SAA1 | Serum amyloid A-1 protein; Amyloid protein A; Serum amyloid protein A(2-104); Serum amyloid protein A(3-104); Serum amyloid protein A(2-103); Serum amyloid protein A(2-102); Serum amyloid protein A(4-101) |
| P0DJI9 | SAA2 | Serum amyloid A-2 protein |

Figure 3:
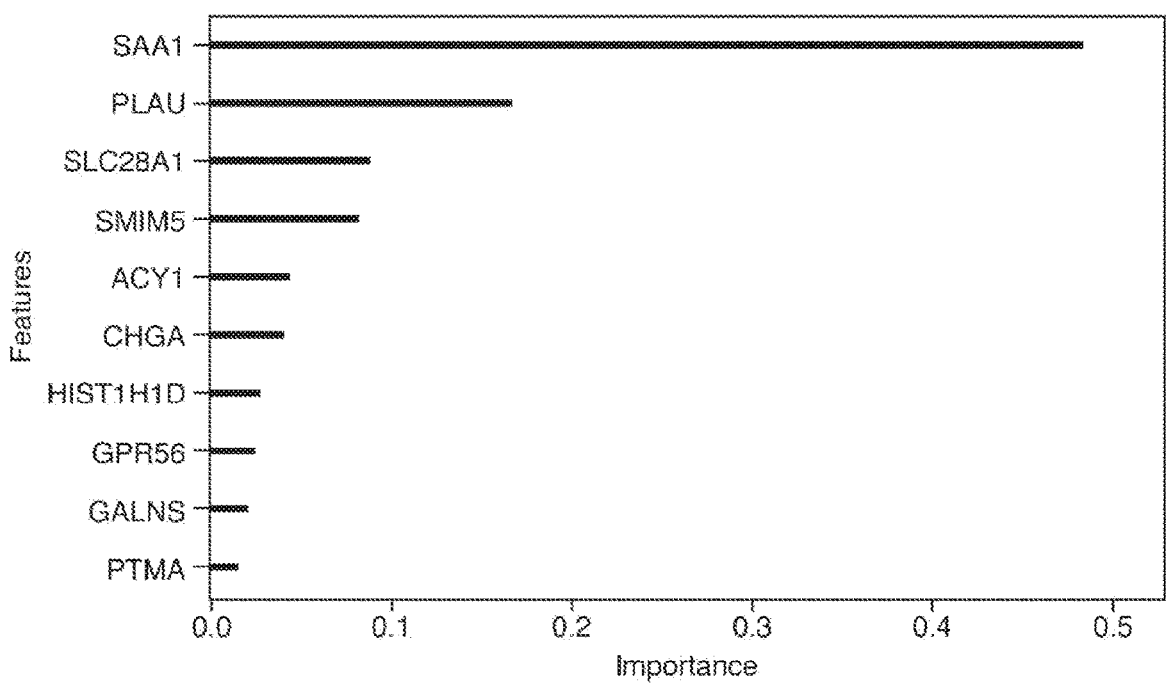
FIG. 3. shows a multi-parameter analysis using the XGBOOST algorithm, that can identify severe systemic inflammation characterized by blood CRP>100 mg/L. The relative importance of each of the urinary biomarkers in the model is indicated.

The analysis was repeated, with a cutoff of blood CRP>100 mg/L as the reference marker. A protein signature capable of distinguishing this patient group from the remaining subjects was identified, as presented in Table 5 FIG. 3 shows the relative importance of each of the urinary biomarkers in the model.

a prediction model demonstrating high correlation with serum CRP levels. The evaluation was done using leave-one-out cross validation, in which the algorithm was sequentially trained on all but one sample, and used to predict the left-out sample. The regularization parameter was chosen using a second nested 10-fold cross validation.

TABLE 5

| markers for severe systemic inflammation (blood CRP >100 mg/L) | | |
|---|---|---|
| Accession No. | Gene | Gene product |
| P0DJI8 | SAA1 | Serum amyloid A-1 protein; Amyloid protein A; Serum amyloid protein A(2-104); Serum amyloid protein A(3-104); Serum amyloid protein A(2-103); Serum amyloid protein A(2-102); Serum amyloid protein A(4-101) |
| P00749 | PLAU | Urokinase-type plasminogen activator; Urokinase-type plasminogen activator long chain A; Urokinase-type plasminogen activator short chain A; Urokinase-type plasminogen activator chain B |
| O00337 | SLC28A1 | Sodium/nucleoside cotransporter 1 |
| Q71RC9 | SMIM5 | Small integral membrane protein 5 |
| Q03154 | ACY1 | Aminoacylase-1 |
| P10645 | CHGA | Chromogranin-A; Vasostatin-1; Vasostatin-2; EA-92; ES-43; Pancreastatin; SS-18; WA-8; WE-14; LF-19; Catestatin; AL-11; GV-19; GR-44; ER-37; GE-25; Serpinin-RRG; Serpinin; p-Glu serpinin precursor |
| P16402 | HIST1H1D | Histone H1.3 |
| Q9Y653 | GPR56 | G-protein coupled receptor 56; GPR56 N-terminal fragment; GPR56 C-terminal fragment |
| P34059 | GALNS | N-acetylgalactosamine-6-sulfatase |
| P06454 | PTMA | Prothymosin alpha; Prothymosin alpha, N-terminally processed; Thymosin alpha-1 |

Accordingly, the results demonstrate the ability to identify patients with high-grade systemic inflammation, requiring medical intervention, in a non-invasive manner.

Example 2. Urine Protein Signature for Monitoring the Inflammatory Status

Figure 4:
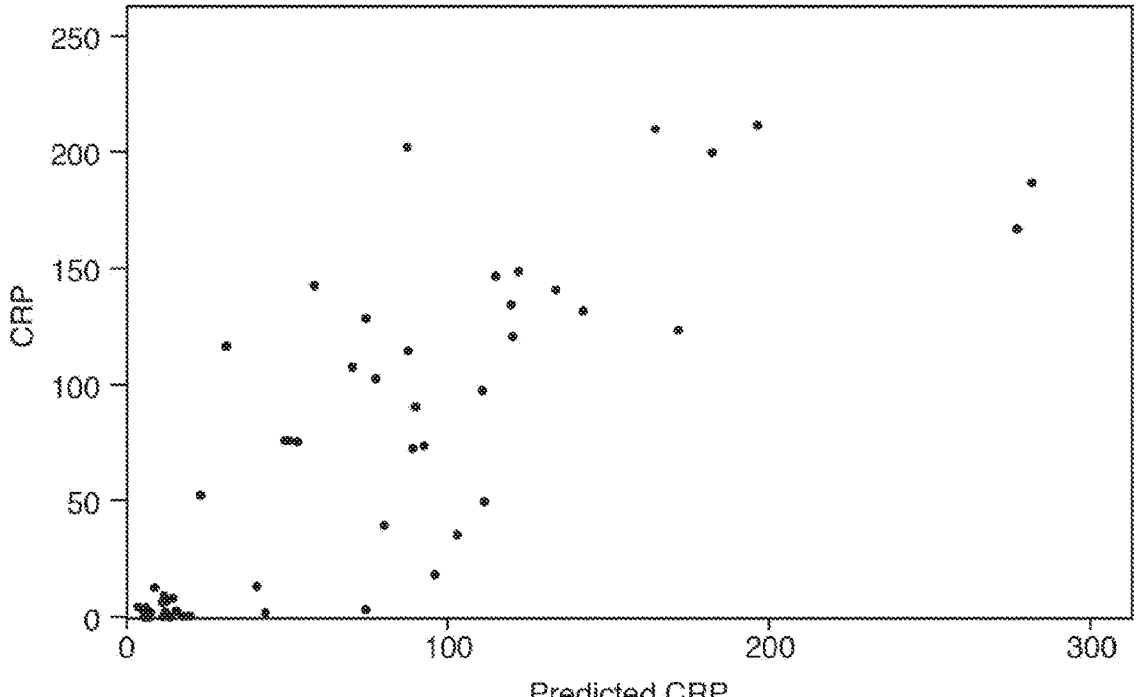
FIG. 4. shows a correlation curve between the measured blood CRP level and the blood CRP level predicted by the urinary biomarker signature.

Using the Lasso algorithm, all the proteins identified in urine in Example 1 were tested for their ability to construct Remarkably, a protein signature was identified, capable of correctly predicting the serum CRP level measured in the test subjects, with a correlation of 0.8 (R-squared 0.64). The details of the signature proteins are listed in Table 6. The correlation curve between the measured blood CRP level and the blood CRP level predicted by the urinary biomarker signature is shown in FIG. 4.

TABLE 6

| Markers for monitoring inflammatory status | | |
|---|---|---|
| Accession No. | Gene | Gene product |
| P01009 | SERPINA1 | Alpha-1-antitrypsin; Short peptide from AAT |
| Q9HBR0 | SLC38A10 | Putative sodium-coupled neutral amino acid transporter 10 |
| P00751 | CFB | Complement factor B; Complement factor B Ba fragment; |

TABLE 6-continued

| Markers for monitoring inflammatory status | | |
|---|---|---|
| Accession No. | Gene | Gene product |
| | | Complement factor B Bb fragment |
| P00740 | F9 | Coagulation factor IX; Coagulation factor IXa light chain; Coagulation factor IXa heavy chain |
| P02741 | CRP | C-reactive protein; C-reactive protein(1-205) |
| Q9Y279 | VSIG4 | V-set and immunoglobulin domain-containing protein 4 |
| Q12805 | EFEMP1 | EGF-containing fibulin-like extracellular matrix protein 1 |
| Q15828 | CST6 | Cystatin-M |
| P02750 | LRG1 | Leucine-rich alpha-2-glycoprotein |
| Q9UHI8 | ADAMTS1 | A disintegrin and metalloproteinase with thrombospondin motifs 1 |
| P0DJI8 | SAA1 | Serum amyloid A-1 protein; Amyloid protein A; Serum amyloid protein A(2-104); Serum amyloid protein A(3-104); Serum amyloid protein A(2-103); Serum amyloid protein A(2-102); Serum amyloid protein A(4-101) |
| P0DJI9 | SAA2 | Serum amyloid A-2 protein |
| Q16661 | GUCA2B | Guanylate cyclase activator 2B; Guanylate cyclase C-activating peptide 2; Uroguanylin |

The results demonstrate the construction of a highly predictive model, capable of assessing the level of systemic inflammation not only in high-grade severe cases, but also in patients exhibiting signs of mild and moderate inflammation. Thus, the results provide for the detection and monitoring of alterations in the level of systemic inflammation, useful e.g. for disease prognosis, for early identification of in discovery mode using mass spectrometry-based proteomics in which the levels of 1,879 proteins were measured, essentially as described in Example 1.

The patient characteristics are summarized it Table 7 below. The infection etiologies and clinical diagnoses of the patients are listed in Table 8 below, along with a summary of tests by which the diagnoses were confirmed.

TABLE 7

| Summary of patient characteristics | | | | | |
|---|---|---|---|---|---|
| Parameter | Bacterial | Viral | p value | Control | p value |
| n | 32 | 26 | | 29 | |
| Age, years (mean ± STD) | 60.0 (17.1) | 49.0 | 0.027 | 43.4 (18.1) | 0.003 |
| Gender, % male | 71.9% | 61.5% | 0.404 | 62.5% | 0.628 |
| Hypertension, % | 53.1% | 30.8% | 0.087 | 6.9% | 0.001 |
| Dyslipidemia, % | 43.8 | 19.2 | 0.048 | 6.9% | 0.003 |
| Diabetes Mellitus, % | 34.4 | 19.2 | 0.199 | 0 | 0.002 |
| Blood CRP, admission | 122.1 (111.1) | 22.5 (21.5) | <0.001 | 1.25 (1.9) | <0.001 |
| | 134.4 (94.7) | 26.1 (27.9) | <0.001 | | |
| Urinalysis Max | 168.5 (112.6) | 30.9 (32.8) | <0.001 | | |
| eGFR, ml/min/1.73 m2 | 85.4 (31.3) | 83.2 (19.3) | 0.744 | 95.4 | 0.240 |
| WBCC, $10^9$/L (mean ± STD) | 13.8 (4.9) | 7.3 (2.8) | <0.001 | 6.3 (1.99) | <0.001 |
| Neutrophil, % | 79.8 (9.7) | 64.5 (17.7) | <0.001 | 53.5 (13.3) | <0.001 |
| Lymphocyte, % | 10.6 (7.2) | 23.4 (15.1) | <0.001 | 31.2 (8.96) | <0.001 |
| Platelets, $10^9$/L (mean ± STD) | 260.7 (92.9) | 183.9 (51.5) | <0.001 | 212.4 (81.8) | 0.001 | subjects that are at enhanced risk of developing disease complications and for evaluating treatment efficacy.

Example 3. Additional Urine Biomarkers for Severe Systemic Inflammation

An additional study was conducted on a second cohort of 380 individuals including healthy human control subjects and patients with various inflammatory and infective conditions. Diagnosis (viral or bacterial infection) was made following data review by 3 or 4 independent physicians. Propensity score method was used to select patients for the proteomic analysis. After best matchings of the groups were made based on age, gender and estimated glomerular filtration (eGFR), subjects in the viral and control groups were 10-16 years younger as compared to those in the bacterial group. Accordingly, 90 samples were prepared and analyzed

TABLE 8

| Patient diagnoses in second cohort | | | |
|---|---|---|---|
| Bacterial infection | | Viral Infection | |
| Count | Diagnosis/Positive test | Count | Diagnosis/Positive test |
| 1 | Abdominal abscess | 1 | Asthma exacerbation |
| 1 | CT | 1 | Clinical diagnosis |
| 1 | Abscess (Axillary) | 1 | Bronchitis |
| 1 | Clinical diagnosis | 1 | Clinical diagnosis |
| 1 | Abscess gluteal | 3 | CMV |
| 1 | Clinical diagnosis | 2 | Positive serology |
| 1 | Bacterial Pharyngitis | 1 | Serology with Seroconversion |
| 1 | Throat culture | 1 | Dengue |
| 7 | Cellulitis | 1 | Serology |
| 6 | Clinical diagnosis | 1 | Fever + headache |

TABLE 8-continued

| | Patient diagnoses in second cohort | | |
|---|---|---|---|
| | Bacterial infection | | Viral Infection |
| Count | Diagnosis/Positive test | Count | Diagnosis/Positive test |
| 1 | Clinical diagnosis + Culture | 1 | Clinical diagnosis |
| 1 | Cellulitis + Infected hematoma | 3 | Gastroenteritis |
| 1 | Clinical diagnosis | 3 | Clinical diagnosis |
| 1 | Cholangitis | 1 | Herpes Zoster V1-2 |
| 1 | Clinical diagnosis + Culture | 1 | Clinical diagnosis |
| 2 | Cholecystitis | 1 | Infectious mononucleosis |
| 2 | Clinical diagnosis + Culture | 1 | Serology |
| 1 | Diverticulitis | 3 | Influenza |
| 1 | Clinical diagnosis | 3 | Clinical diagnosis + PCR |
| 1 | Empyema | 4 | Influenza A |
| 1 | Pleurocentesis | 3 | Clinical diagnosis + PCR |
| 1 | Gangrenous cholecystitis | 1 | PCR |
| 1 | Clinical diagnosis + CT + pathology | 1 | Measles |
| 1 | Liver abscess | 1 | Clinical diagnosis + serology |
| 1 | Clinical diagnosis + Culture | 1 | Meningitis Aseptic |
| 1 | Lung Abscess | 1 | Clinical diagnosis + CSF PCR |
| 1 | Osteomyelitis | 2 | URTI |
| 1 | Clinical diagnosis + wound culture + X-ray | 2 | Clinical diagnosis |
| 1 | Parotitis | 2 | Viral Bronchitis |
| 1 | Clinical diagnosis + Culture | 1 | Clinical diagnosis + PCR |
| 7 | Pneumonia | 1 | PCR |
| 1 | Clinical + CXR + CT | 1 | Viral infection |
| 1 | Clinical diagnosis + CT | 1 | Clinical diagnosis |
| 5 | Clinical diagnosis + CXR | 1 | Viral meningitis |
| 29 | Sum | 1 | PCR |
| | | 2 | VZV |
| | | 1 | Clinical diagnosis |
| | | 1 | Clinical diagnosis + PCR |
| | | 1 | VZV |
| | | 1 | PCR |
| | | 30 | Sum |

Based on the proportions of samples in each group that had detectable levels of each protein, gene products in which the difference in detection proportions was the most significant (after filtering proteins with less than 3 peptides in the LC-MS) were selected for further analysis. For the analysis the Lasso algorithm was used, as implemented in the R package glmnet, with L-1 penalty (alpha=1). The shrinkage parameter (lambda) was selected using cross-validation.

Figure 5:
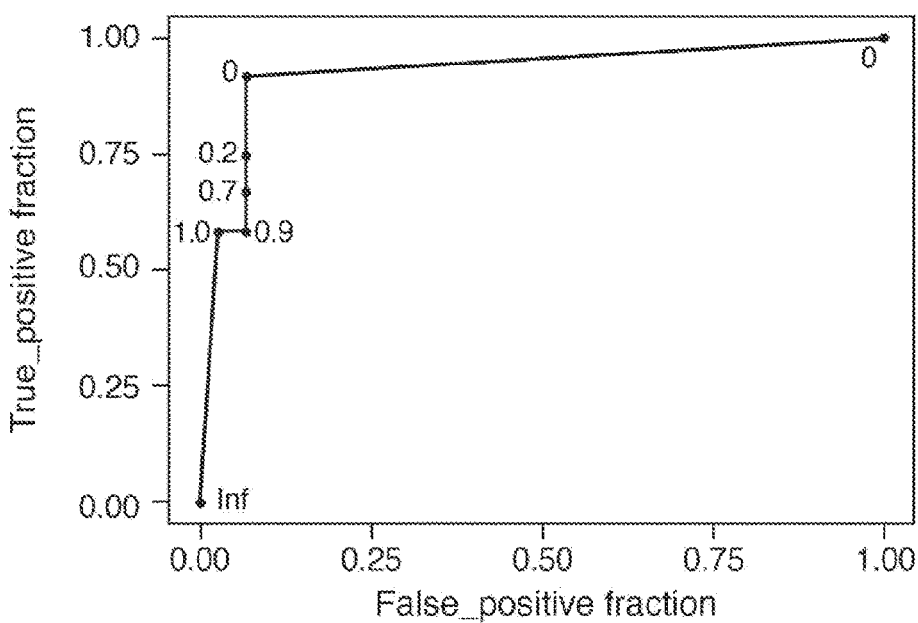
FIG. 5. presents a receiver operating characteristic (ROC) curve for the identification of severe systemic inflammation characterized by blood CRP>100 mg/L using urinary protein markers SRGN, IGLV3-12, and ASGR1.

Remarkably, a protein signature of three proteins, namely SRGN, IGLV3-12, and ASGR1 gene products (Table 9 below), was able to discriminate patients with severe systemic inflammation, characterized by blood CRP>100 mg/L, and the remaining subjects. As can be seen in FIG. 5, the signature was able to identify all of the patients with blood CRP>100, with only 5% false positive readings.

TABLE 9

| markers for severe systemic inflammation (blood CRP >100 mg/L) | | |
|---|---|---|
| Accession No. | Gene | Gene product |
| P10124 | SRGN | Serglycin |
| P07306 | ASGR1 | Asialoglycoprotein receptor 1 |
| A0A075B6K2 | IGLV3-12 | Human Immunoglobulin lambda variable 3-12 |

Figure 6:
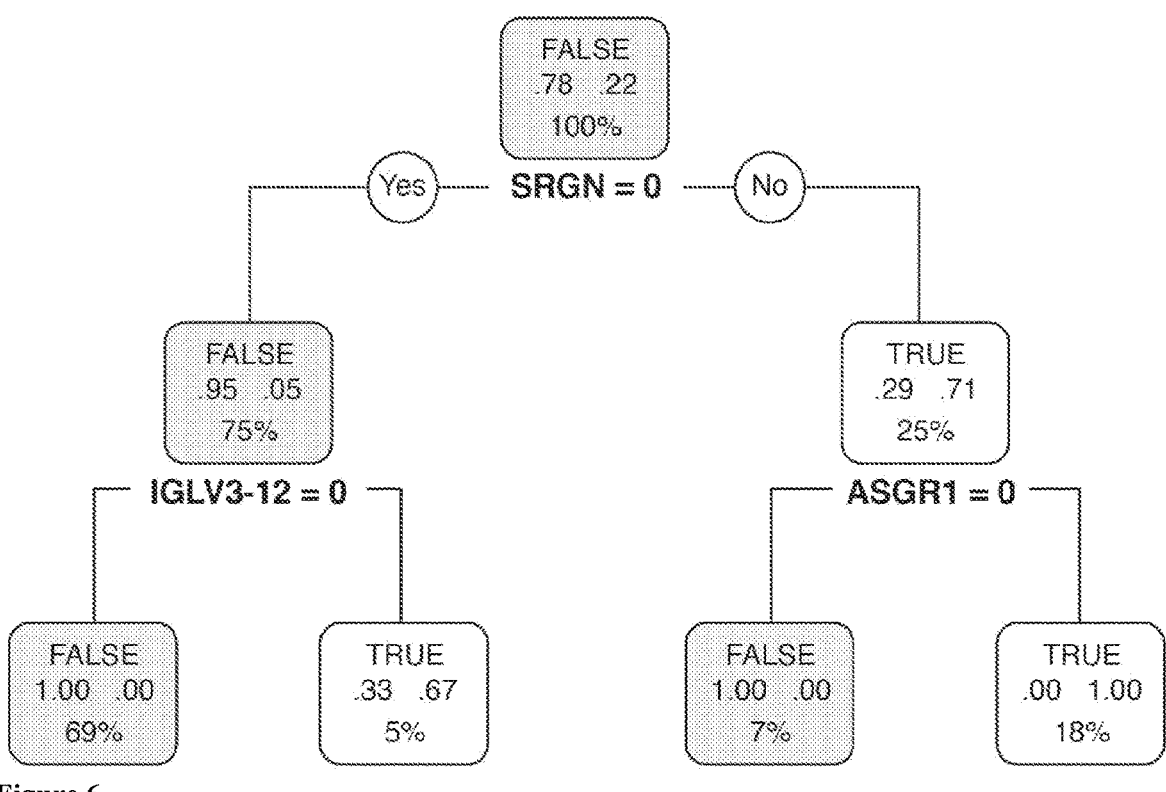
FIG. 6. shows a decision tree analysis for the identification of severe systemic inflammation characterized by blood CRP>100 mg/L using urinary protein markers SRGN, IGLV3-12, and ASGR1.

Further, FIG. 6 presents a decision tree analysis demonstrating detection of severe systemic inflammation characterized by blood CRP>100 mg/L using the gene products listed in Table 9. In FIG. 6, each split represents a decision criterion, as described in the text below the node. The color of each node represents the ratio of patients with blood CRP>100 included in this criterion, going from white (severe systemic inflammation) to dark (representing the remaining test subjects, also referred to herein as "low inflammation"). In each box, the upper text indicates where most people in this leaf are (False—most people in the leaf are not inflamed, True—most people are inflamed). The two decimal numbers represent the proportion of healthy/low inflammation (on the left side), or severe systemic inflammation (right side), respectively, of the overall population in the node. The lowest number represents the proportion of the overall population falling in this node. Branches were hierarchically organized, such that the higher is more important.

As can be seen in FIG. 6, the top box describes the whole cohort in which 78% of the subject have blood CRP levels <100 mg/L; and 22% of the subjects have blood CRP<100 mg/L. The first leaf criterion is based on the absence of urine SRGN, wherein the left side represents 75% of the whole population who have no detectable level of SRGN. In this group, 95% of the subjects belong to the low inflammation group. On the other size (right) are subjects with detectable urine SRGN, presenting a 71% chance to have severe systemic inflammation. The last leaf divides the groups based on the absence on IGLV3-12 or ASGR1.

As can be seen, the presence of these gene products in urine, namely SRGN, IGLV3-12 and ASGR1, is positively correlated with severe systemic inflammation. As can be further seen, hierarchical clustering with the urinary markers, starting with SRGN as the highest-ranking parameter was highly correlated with the analysis based on blood CRP levels. Taken together, the results demonstrate that it is possible to correctly identify patients as having or not having severe systemic inflammation using decision tree analysis of urinary markers SRGN, IGLV3-12 and ASGR1, with high accuracy.

Example 4—Additional Proteomic Signature for Monitoring Inflammatory Status

Regularized regression (glmnet) was applied to all the proteins identified in urine in Example 3. To this end, Lasso regression of the blood CRP value against the urine protein values was performed, where the shrinkage parameter was increased until a small subset of proteins remains.

Tables 10 to 14 show the details of gene product signatures, identified as being capable of correctly predicting the serum CRP level measured in the test subjects in a continuous manner, as detailed below. The beta coefficients, representing the contribution of each marker to the predicted CRP level, are also presented.

In particular, the gene products listed in Table 10 represent a urinary signature of 12 gene products, providing a linear correlation with blood CRP in all the test subjects (r=0.92).

TABLE 10

Markers for obtaining and monitoring inflammatory status

| Gene | Gene product | Beta coefficient |
|---|---|---|
| GPC4 | Glypican-4 | −5.894e−8 |
| SERPINA3 | Alpha-1-antichymotrypsin; Alpha-1-antichymotrypsin His-Pro-less | 6.727621e−09 |
| LRG1 | Leucine-rich alpha-2-glycoprotein | 1.229088e−08 |
| ORM1 | Alpha-1-acid glycoprotein 1 | 4.554602e−10 |
| CTSH | Pro-cathepsin H; Cathepsin H mini chain; Cathepsin H; Cathepsin H heavy chain; Cathepsin H light chain | 2.053125e−07 |
| S100A1 | Protein S100-A12; Calcitermin | 5.202901e−06 |
| ASAH1 | Acid ceramidase; Acid ceramidase subunit alpha; Acid ceramidase subunit beta | 2.368168e−07 |
| PTGR1 | Prostaglandin reductase 1 | 3.492739e−07 |
| ATP6AP1 | V-type proton ATPase subunit S1 | 6.136674e−07 |
| MYOZ1 | Myozenin-1 | 6.541453e−06 |
| ABRACL | Costars family protein ABRACL | 2.866362e−06 |
| TLN1 | Talin-1 | 1.006058e−09 |

Next, a group of patients with systemic inflammation characterized by blood CRP levels are higher than 30 mg/L was selected for further analysis. The gene products listed in Tables 11 and 12 represent urinary signatures of 15 and 5 gene products, respectively, capable of correctly predicting the serum CRP level in these patients, with high correlation (r=0.95 and 0.83, respectively). Thus, these markers are thus particularly useful to assess moderate and severe systemic inflammation.

TABLE 11

Markers for evaluating higher levels of systemic inflammation

| Gene | Gene product | Beta coefficient |
|---|---|---|
| GPC4 | Glypican-4; Secreted glypican-4 | −1.48E−06 |
| SERPINA3 | Alpha-1-antichymotrypsin; Alpha-1-antichymotrypsin His-Pro-less | 2.06E−09 |
| IL2RA | Interleukin-2 receptor subunit alpha | 2.26E−06 |
| LRG1 | Leucine-rich alpha-2-glycoprotein | 1.54E−09 |
| UMOD | Uromodulin; Uromodulin, secreted form | −1.24E−09 |
| CTSH | Pro-cathepsin H; Cathepsin H mini chain; Cathepsin H; Cathepsin H heavy chain; Cathepsin H light chain | 1.03E−07 |
| C1S | Complement C1s subcomponent; Complement C1s subcomponent heavy chain; Complement C1s subcomponent light chain | −4.46E−10 |
| EZR | Ezrin | 1.44E−07 |
| DDT; DDTL | D-dopachrome decarboxylase; D-dopachrome decarboxylase-like protein | 1.20E−05 |
| HNRNPA3 | Heterogeneous nuclear ribonucleoprotein A3 | −9.12E−07 |
| FCN2 | Ficolin-2 | 1.07E−06 |
| MYH14 | Myosin-14 | 2.18E−06 |
| CD177 | CD177 antigen | 4.38E−07 |
| MYOZ1 | Myozenin-1 | 8.05E−06 |
| FCGBP | IgGFc-binding protein | −2.25E−06 |

TABLE 12

Markers for evaluating higher levels of systemic inflammation

| Gene | Gene product | Beta coefficient |
|---|---|---|
| LRG1 | Leucine-rich alpha-2-glycoprotein | 4.57E−09 |
| UMOD | Uromodulin; Uromodulin, secreted form | −2.22E−10 |
| DDT; DDTL | D-dopachrome decarboxylase; D-dopachrome decarboxylase-like protein | 1.04E−05 |
| FCN2 | Ficolin-2 | 3.91E−08 |
| MYOZ1 | Myozenin-1 | 2.67E−06 |

Further, the ability to predict the level of inflammation based on the presence or absence of markers, rather than their amount, was evaluated. Tables 13 and 14 below represent urinary signatures of 9 and 5 gene products, respectively, capable of correctly predicting the serum CRP level using this methodology, with high correlation (r=0.94 and 0.8, respectively).

TABLE 13 signature for evaluating systemic inflammation based on presence or absence of 9 urine markers

| Gene | Gene product | Beta coefficient |
|---|---|---|
| IGKV2-29 | Immunoglobulin kappa variable 2-29 | −1.617387 |
| MATN4 | Matrilin-4 | −42.12507 |
| LGALS1 | Galectin-1 | 26.28549 |
| C1S | Complement C1s subcomponent; Complement C1s subcomponent heavy chain; Complement C1s subcomponent light chain | −5.7029 |
| HLA-DPA1 | HLA class II histocompatibility antigen, DP alpha 1 chain | 12.52201 |
| NEB | Nebulin | −10.07096 |
| CRHBP | Corticotropin-releasing factor-binding protein | 33.26439 |
| GSTO1 | Glutathione S-transferase omega-1 | 9.035954 |
| DLK1 | Protein delta homolog 1; Fetal antigen 1 | −9.503489 |

TABLE 14 signature for evaluating systemic inflammation based on presence or absence of 5 urine markers

| Gene | Gene product | Beta coefficient |
|---|---|---|
| MATN4 | Matrilin-4 | −28.38477 |
| LGALS1 | Galectin-1 | 9.659388 |
| CRHBP | Corticotropin-releasing factor-binding protein | 36.61007 |
| DLK1 | Protein delta homolog 1; Fetal antigen 1 | −0.403149 |
| MYOZ1 | Myozenin-1 | 5.738796 |

Example 5. Newly-Identified SAA Fragments as Urinary Markers for Inflammation A series of experiments to characterize the amino acid sequence of the SAA1 and SAA2 gene products identified in the urine samples. To this end, peptidomic analyses were performed on urine samples from patients described in Example 3. The samples were filtered with 10 kDa molecular weight cutoff membranes, and the low molecular weight fraction was collected. It was then desalted using C18 cartridges and analyzed by mass spectrometry.

Unexpectedly, it was found that both SAA1 and SAA2 are present in the samples as endogenous peptides, and not whole proteins. The SAA1 and SAA2 fragments were characterized by N' truncations ranging beyond the signal peptide.

Remarkably, one of the peptides, namely the SAA2-derived peptide GNYDAAKRGPGGAW (SEQ ID NO: 1), exhibited high correlation (0.78) with blood CRP levels. Accordingly, this unique and newly-identified peptide may be used in embodiments of the invention as a marker for inflammation.

Example 6. Known Blood Markers are not Identified in Urine

The levels of TRAIL, CXCL10 (IP-10) and CRP were further measured in urine samples of healthy subjects and of subjects afflicted with various infections, essentially as described in Example 3. The targeted proteomic experiment was performed on a total of 91 samples: 32 healthy controls, the levels of their urine counterparts, including those hitherto suggested or recognized as diagnostic biomarkers when measured in blood. In contradistinction, detectable and consistent levels compatible with use as urinary biomarkers were unexpectedly characteristic of the selected gene products and diagnostic signatures of the invention.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

```
                      SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: synthetic peptide

<400> SEQUENCE: 1

Gly Asn Tyr Asp Ala Ala Lys Arg Gly Pro Gly Gly Ala Trp
1               5                   10
``` and 59 samples from patients with inflammatory conditions (30 with viral infections, and 29 with bacterial infections).

Gene products corresponding to CRP were detected in the urine samples as follows: 14 out of the 32 control samples (43.8%), 26 out of the 30 viral samples (86.7%) and 28 out of the 29 bacterial samples (96.6%) contained a CRP gene product. The increased abundance of urinary CRP in patients with inflammatory conditions compared to healthy subjects reached statistical significance (Chi square <0.001); no statistical significance was reached when comparing subjects with viral infections to those with bacterial infections (Chi square p=0.173). When comparing the levels of urinary CRP in the three groups, a significant difference was identified between patients with inflammatory conditions and healthy controls (median IQR in controls: 0 [0-1,771,063], in viral infections: 6,191,530 [1,742,375-14,390,560] and in bacterial infections 15,081,115 [2,886,969-47,985,575], p<0.001, Kruskal-Wallis H test). The difference between viral and bacterial patients did not remain significant following correction for multiple comparisons (p=0.011, Mann-Whitney Test for comparison between viral and controls).

In striking contradistinction, TRAIL and CXCL10 gene products were both undetectable in any of the urine samples. In other words, despite their reported abundance in blood samples, including in subjects with various infections, no TRAIL or CXCL10 gene products could be measured in the urine of healthy subjects or of either of the patient groups.

Thus, the results exemplify the lack of correlation that is typically observed between the levels of blood proteins and

The invention claimed is:

1. A method for treating a patient with an anti-inflammatory drug, the method comprising the steps of:

determining whether the patient has systemic inflammation by:

obtaining a urine sample from the patient; and performing an immunoassay on the urine sample to determine if the urine sample has a presence of a peptide fragment having the amino acid sequence set forth in SEQ ID NO: 1—GNYDAAKRGPG-GAW thereby providing a urinary proteomic signature of the patient, wherein the immunoassay comprises subjecting the urine sample to antibodies specific to the peptide fragment, and wherein the patient is administered with an anti-inflammatory drug if the urinary proteomic signature of the patient corresponds to a control urinary proteomic signature of subjects suffering from the systemic inflammation; and wherein the patient is not administered with the anti-inflammatory drug if the urinary proteomic signature of the patient does not correspond to the control urinary proteomic signature.

2. The method of claim 1, wherein the control urinary proteomic signature is obtained from mass-spec analysis of urine samples obtained from a plurality of subjects suffering from systemic inflammation.

3. The method of claim 1, wherein the immunoassay is a lateral flow test.

4. The method of claim 1, wherein determining the presence of the peptide fragment comprises determining a level of the peptide fragment in the urine sample.

5. The method of claim 4, further comprising comparing the determined level of the peptide fragment to a predetermined cutoff value.

* * * * *